(12) United States Patent
McLean

(10) Patent No.: US 6,858,589 B2
(45) Date of Patent: *Feb. 22, 2005

(54) METHODS OF AND COMPOSITIONS FOR POTENTIATING THE ACTION OF AGENTS ACTIVE ON CELL WALL SITES OF THE SUSCEPTIBLE BACTERIA

(75) Inventor: Allan Joseph McLean, Jericho (AU)

(73) Assignee: Pharmacy and Therapeutic Advisory Consultancy Pty LTD, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/200,201

(22) Filed: Jul. 23, 2002

(65) Prior Publication Data

US 2003/0096766 A1 May 22, 2003

Related U.S. Application Data

(63) Continuation-in-part of application No. 09/117,105, filed as application No. PCT/AU97/00040 on Jan. 24, 1997, now Pat. No. 6,475,992.

(30) Foreign Application Priority Data

Jan. 25, 1996 (AU) .............................................. PN7715

(51) Int. Cl.$^7$ .......................... A01N 43/04; A61K 31/70
(52) U.S. Cl. ............................. 514/37; 514/36; 514/38; 514/39; 536/13.6; 536/16.8; 536/4.1
(58) Field of Search ................................ 536/13.6, 6.8, 536/4.1; 514/36–42

(56) References Cited

U.S. PATENT DOCUMENTS

| | | |
|---|---|---|
| 3,536,809 A | 10/1970 | Appleweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,710,384 A | 12/1987 | Rotman |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 6,106,858 A * | 8/2000 | Ye et al. ...................... 424/450 |
| 6,475,992 B2 * | 11/2002 | McLean ....................... 514/37 |

OTHER PUBLICATIONS

Weinstein et al., "Cephalosporin–Aminoglycoside Synergism in Experimental Enterococcal Endocarditis", Antimicrobial Agents and Chemotherapy, Jun. 1976, p. 983–987.*

O'Kane, G.M., Gottlieb, T & Bradbury, R. (1998). Staphylococcal bacteraemia: the hospital or the Home? A review of *Staphylococcus aureus* bacteraemia at Concord Hospital in 1993. *Australia and New Zealand Journal of Medicine*. 28, 23–27.

Rosenberg, J. (1995). Methicillin–resistant *Staphylococcus auresus* (MRSA) in the community: who's watching? *The Lancet*, 346, 132–133.

Pate, K.R., Nolan, R.L., Bannerman, R.I.& Feldman, S. (1995). Methicillin–resistant *Staphylococcus aureus* in the community. *The Lancet*, 346, 978.

Boyce, J.M.(1998). Are the epidermioligy and microbiology of methicillin–resistant *Staphylococcus aureus* changing? *JAMA*, 279(8),623–624.

Herold, B.C. Immergluck, L.C., Maranan, M.C., Lauderdale, D.S., Gaskin, R.E., Boyle–Vavra, S., Leitch, C.D. and Daum, R.S. (1998). Community–acquired methicillin–resistant *Staphylococcus aureus* in children with no identified predisposing risk. *Journal of the American Medical Association*, 279(8), 593–598.

Lindenmayer, J.M., Schoenfeld, S. O'Grady, R. and Carney, J.K. (1998). Methicillin–resistant *Staphylococcus aureus* in a high school wrestling team and the surrounding community. *Archives of Internal Medicine*, 158, 895–899.

Moreno, F., Crisp, C., Jorgensen, J.H. & Patterson, J.E. (1995). Methicillin–resistant *Staphylococcus aureus* as a community organism. *Clinical Infectious Diseases*, 21, 1308–12.

Steinberg, J.P., Clark, C.C. and Hackman, B.O. (1996). Nosocomial and community–acquired *Staphylococcus aureus* bacteremias from 1980 to 1993: impact of intravascular devices and methicillin resistance. *Clinical Infectious Diseases*, 23, 255–259.

Akram, J.& Glatt, A.E. (1998). True community–acquired methicillin–resistant *Staphylococcus aureus* bacteremia. *Infection Control and Hospital Epidemiology*, 19(2), 106–107.

Kayaba, H., Kodama, K., Tamura, H. & Fujiwara, Y. (1996). The spread of methicillin–resistant in a rural community: will it become a common microorganism colonizing among the general population? *Surgery Today*, 27, 217–219.

Mitchell, J.M. MacCulloch, D. & Morris, A.J. (1996). MRSA in the community. *New Zealand Medical Journal*, 109(1032), 411.

(List continued on next page.)

Primary Examiner—James O. Wilson
Assistant Examiner—Traviss C. McIntosh, III
(74) Attorney, Agent, or Firm—Stites & Harbison PLLC; B. Aaron Schulman

(57) ABSTRACT

The invention provides a method of potentiating the activity of antibacterial agents that act on bacterial cell walls, comprising the step of administering to a subject an antibacterial agent and an aminoglycoside to attain a peak concentration of at least 4 mg/l of aminoglycoside and thereafter maintaining the aminoglycoside at a concentration of up to 4 mg/l for at least 1 hour. Compositions comprising an antibacterial agent and an aminoglycoside for efficacious treatment of bacterial infection are also provided.

12 Claims, 9 Drawing Sheets

OTHER PUBLICATIONS

Maguire, G.P., Arthur, A.D., Boustead, P.J., Dwyer, B. & Currie, B.J. (1996). Emerging epidemic of community-acquired methicillin-resistant *Staphylococcus aureus* infection in the Northern Territory. *Medical Jouranl of Australia*, 164, 721–723.

Riley, T.V., Pearman, J.W. and Rouse, I.L.(1995). Changing Epidemiology of methicillin-resistant *Staphylococcus aureus* in Western Australia. *The Medical Journal of Australia*, 163, 412–414.

Collignon, P., Gosbell, I., Vickery, A., Nimmo, G., Stylianopoulos, T., & Gottlieb, T (1998). Community-acquired methicillin-resistant *Staphylococcus aureus* in Australia. *The Lancet*, 352, 145–146.

Maguire, G.P., Arthur, A.D., Boustead, P.J., Dwyer, B. and Currie, B.J. (1998). Clinical experience and outcomes of community-acquired and nosocomial methicillin-resistant *Staphylococcus aureus* in a northern Australian hospital. *Journal of Hospital Infections*, 38, 273–281.

Daum, R.S. (1998). Community-acquired methicillin-resistant *Staphylococcus aureus* infections. *Concise Reviews of Pediatic Infectious Diseases*, 17(8), 745–747.

Fogel, M.A., Nussbaum, P.B., Feintzeig, I.D. Hunt, W.A., Gavin, J.P. and Kim, R.C. (1998). Cephazolin in chronic hemodialysis patients: a safe, effective alternative to vancomycin. *American Journal of Kidney Diseases*, 32(3), 401–409.

Bastone, E.B., Li, S.C., Ioannides–Demos, L.L., Spicer, W.J. & McLean, A.J. (1993). Kill kinetics and regrowth patterns of *Eschericia coli* exposed to gentamicin concentrationtime profiles simulating in vivo bolus and infusion dosing. *Antimicrobial Agents and Chemotherapy*, 37(4), 914–917.

Begg. E.J. & Barclay, M.L. (1995). Aminoglycosides– 50 years. *British Journal of Clinical Pharmacology.* 39, 597–603.

Wood, P.J., Ioannides–Demos, L.L., Bastone, E.B., Spicer, W.J. & McLean, A.J. (1996). Kill kinetics and regrowth patterns of *Pseudomonas aeruginosa* exposed to concentration–time profiles of tobramycin simulating in vivo infusion and bolus dosing. *Antimicrobial Agents and Chemotherapy*, 40(5), 1321–1324.

Ali, M.Z. & Goetz, M.B. (1997). A meta–analysis of the relative efficacy and toxicity of single daily dosing versus multiple daily dosing of aminoglycosides. *Clionical Infectious Diseases* 24, 796–809.

Moore, R.D., Lietman, P.S.& Smith, C.R. (1987). Clinical response to aminoglycoside therapy: importance of the ratio of peak concentration to minimal inhibitory concentration. *The Journal of Infectious Diseases*, 155(1), 93–99.

Gerber, A.U,., Wiprachtiger, P., Stettler–Spichiger, U. & Lebek, G. (1982). Constant infusions vs. intermittent doses of gentamicin against *Pseudomonas aeruginosa* in–vitro. *The Journal of Infectious Diseases*, 145(4), 554–560.

Rayner, C.R., Ioannides–Demos, L.L, Brien, J.E., Lioloios, L.L. & Spicer, W.J. (1998). Initial concentration–time profile of gentamicin determines efficacy against *Enterobacter cloacas* ATCC 13047. *Antimicrobial Agents and Chemotherapy*, 42(6), 1370–1374.

Ioannides–Demos, L.L., Liolios, L.L., Wood, P., Spicer, W.J. & McLean, A.J. (1998). Changes in MIC alter responses to *Pseudomonas aeruginose* to tobramycin exposure. *Antimicrobial Agents and Chemotherapy*, 42(6)1365–1369.

Ter Braak, E.W., De Vries, P.J., Boutler, K.P., Van Der Vegt, S.G., Dorrestein, G.C., Nortier, J.W., Van Dijk, A., Verkooyen, R.P. & Verbrugh, H.A. (1990). Once–daily dosing regimen for aminoglycoside plus β–lactam combination therapy of serious bacterial infections: comparative trial with netilmicin plus ceftriaxone. *American Journal of Medicine*, 89, 58–65.

Kapusnik, J.E., Hackbarth, C.J., Chambers, H.F., Carpenter, T & Sande, M.A. Single, larger, daily dosing versus ontermittent dosing of toramycin for treating experimental *Pseudomonas pneumonia. Journal of Infectious Diseases*, 158(1), 7–12, 1988.

Gavalda, J., Cardona, P.J., Almitrante, B., Capdevila, A.J., Laguarda, M., Pou, L., Crespo, E., Pigrau, C. & Pahissa, A. (1996). Treatment of experiemntal endocarditis due to *Enterococcus faecalis* using once–daily dosing regimen of gentamicin plus simulated profiles of ampicillin human serum. *Antimicrobial Agents and Chemotherapy*, 40(1), 173–178.

Bailey, R.R., Begg, E.J., Smith, A. H., Robson, R.A., Lynn, K.L., Chambers, S.T., Barclay, M.L. & Hornibrook, J. (1996). Prospective, randomized, controlled study comparing two dosing regimens of gentamicin/oral ciprofloxacin switch therapy for acute pyelonephritis. *Clinical Nephrology*, 46(3), 183–186.

Bailey, T.C., Little, J.R., Littenberg, B., Reichley, R.M. & Dunagan, W.C. (1997). A meta–analysis of extended–internal dosing versus multiple daily dosing of aminoglycosides. *Clinical Infectious Diseases*, 24, 786–795.

Cholewka, K.A., Ioannides–Demos, L.L., Liolios, L., Paull, P., Spicer, W.J., and McLean, A.J. (1999).Caphelosporin clinical concentration–time profile modelling and in–vitro bactericidal effects on *Escherichia coli*. Journal of Antimicrobial Chemotherapy, 44, 471–476.

\* cited by examiner

METHODS OF AND COMPOSITIONS FOR POTENTIATING THE ACTION OF AGENTS ACTIVE ON CELL WALL SITES OF THE SUSCEPTIBLE BACTERIA

CROSS-REFERENCE TO RELATED APPLICATIONS

This application is a continuation-in-part of U.S. patent application Ser. No. 09/117,105, filed Aug. 28, 1998 now U.S. Pat. No. 6,475,992. Which is a 371 of PCT/AU97/00040 filed Jan. 24, 1997.

FIELD OF THE INVENTION

The present invention relates to a method of potentiating the activity of an antibacterial agent by using an aminoglycoside, and to novel compositions comprising an antibacterial agent and an aminoglycoside. It also relates to a method of treating bacterial infection by administration of the composition of the invention. More particularly, the invention relates to the use of an aminoglycoside to potentiate the activity of antibacterial agents acting at or near cell wall sites, such as β-lactams or cephalosporins. The invention also contemplates optimisation of the efficacy of aminoglycosides. Even more particularly, the invention relates to the use of an aminoglycoside and a β-lactam in treating Gram-positive and Gram-negative bacterial infection.

BACKGROUND OF THE INVENTION

A major problem in treatment of infections caused by bacteria, particularly hospital acquired infections, is that an increasing number of bacteria are becoming resistant to antibiotics. For example, many strains of *Staphylococcus* and *Enterococcus* are now resistant to most of the currently-available antibiotics. Other organisms, such as *Pseudomonas*, respond poorly. This problem is exacerbated by the ability of many bacteria to transfer resistance to other species of bacteria.

An example of such a bacterium is methicillin resistant *Staphylococcus aureus* (MRSA) which is a recognised problem in hospitals throughout the world. The mechanism of methicillin resistance is not via β-lactamase production but via altered penicillin binding proteins especially through an alteration in PBP2a. All β-lactams (penicillins, cephalosporins and carbapenems) are therefore ineffective which severely limits the choice of effective antibiotic therapy. Additionally hospital strains of MRSA are usually multi resistant. Often glycopeptides such as vancomycin may be the only effective therapy.

Traditionally the acquisition of such infections was associated with recognised risk factors. These included patients with previous antibiotic use (usually with broad spectrum antimicrobials), previous hospitalisation or exposure to healthcare facilities, those with serious illness, exposure to invasive or surgical procedures or the presence of indwelling catheters and IV drug abuse. Recently, there have been an increasing number of infections caused by MRSA which have been acquired in the community (cMRSA). Most of these patients have none of the classical risk factors associated with such infections. Initially the emergence of cMRSA was in isolated communities, but is now found in nearly all capital cities in Australia (Collignon et al., 1998). It has also been reported in many areas including across the U.S. and Canada, Japan, and New Zealand as well as Australia (Rosenberg, J., 1995; Boyce, J. M., 1998; Herold, B. C. et al., 1998; Lindenmayer, J. M. et al., 1998; Moreno, F. et al., 1995). Community acquired strains of MRSA also differ markedly to hospital acquired strains in their antibiotic sensitivity patterns. In the laboratory testing of resistant bacteria, a requirement for concentrations of antibiotics which are higher than the reported minimum inhibitory concentration (MIC) to inhibit the growth of the organisms is often seen.

One group of antibiotics which are clinically becoming less useful due to acquired resistance are the cephalosporins. Cephalosporins are conventionally believed to act at surface sites on the bacterial cell wall at or near the enzymes responsible for cell wall synthesis. For example in Gram-negative organisms with an outer cell wall, the action of cephalosporins is limited by access to these surface sites in the inner cell wall because of molecular size and other determinants of ability to penetrate porin structures in the outer cell wall, and by the action of enzymes (cephalosporinases) which break down the cephalosporins. These cephalosporinases are largely responsible for the emerging clinical resistance of bacteria to cephalosporins.

Aminoglycoside antibiotics are another class of antibiotics that are affected. While the antibiotics are active against a wide spectrum of organisms, their use has been severely limited by the toxic side effects which occur at the doses required to achieve the desired antibacterial effect.

Thus, there is a need to improve the efficacy of antibiotics, particularly cephalosporins. There is also a need to reduce the toxicity of aminoglycoside antibiotics, particularly gentamicin.

It has conventionally been thought that aminoglycosides exert their antibacterial effects via a strictly intracellular mechanism involving inhibition of ribosomal activity. However, the present inventor has examined data on uptake of radioactively—labelled aminoglycosides, and now proposes that aminoglycosides also act at the cell surface so as to contribute to the process of entry into the cell. Thus the hypothesis underlying the present invention is that an important part of the action(s) of aminoglycoside antimicrobials involve creation of breaches in external cell walls of bacteria and in other external capsular layers or membranes composed of lipopolysaccharide or mucopolysaccharide constituents.

It was thought by the present inventor:

1. that the exposure profiles necessary for this action of aminoglycosides were likely to differ from the concentration-time profiles found to apply to intracellular effect(s), and that novel exposure profiles might be identified which would allow avoidance of toxicity on mammalian systems;
2. that the breaches in external cell walls and capsular membranes and layers of bacteria could facilitate entry and access to sites of action of other antibiotics such as cephalosporins which acted at or near cell surfaces, and additionally, that enzyme degradation of antibiotics (e.g. cephalosporinases) might be by-passed.

It has now been surprisingly found that the activity of β-lactam antibiotics, including cephalosporins, can be potentiated by the use of a non-toxic amount of an aminoglycoside antibiotic.

While cMRSA strains are resistant to all β-lactams they are still usually sensitive to erythromycin, tetracycline, trimethoprim, ciprofloxacin and gentamicin (Collignon, P. et al., 1998; Daum, R. S. 1998). We have surprisingly found that the combination of gentamicin with a β-lactam provides an effective empiric treatment program for serious infections caused by such organisms while awaiting sensitivity results.

This combination also avoids the over use of vancomycin and therefore lowers the risk of developing and spreading vancomycin resistant strains of *Staphylococcus aureus* that have now been seen in small but increasing numbers in many areas around the world.

The studies detailed herein, using gentamicin, tobramycin, cephazolin and flucloxacillin demonstrate that the concentration-time profiles producing the cell surface effect involve relatively prolonged exposures over many hours, at lower concentrations than those normally used clinically, where rapid onset (bolus) of high concentration exposure has been the characteristic approach to clinical dosing.

The potentiation of cephalosporin action by degrees in excess of 100 fold was also a surprising finding and suggests high efficiency of cell wall porin as exclusion barriers and enzymatic (cephalosporinase) destruction of cephalosporins.

SUMMARY OF THE INVENTION

In a first aspect, the invention provides a method of potentiating the activity of an antibacterial agent active on bacterial cell wall, comprising the step of administering to a subject in need of such treatment said antibacterial agent and an aminoglycoside in an amount effective to attain a peak concentration of at least 4 mg/l of the aminoglycoside, and thereafter maintaining the aminoglycoside at a concentration of up to 4 mg/l for at least 1 hour.

In a second aspect, the invention provides an antibacterial composition in sustained-release formulation, comprising an aminoglycoside and an antibacterial agent, wherein the formulation is capable of potentiating the activity of an antibacterial agent active on bacterial cell wall such that the aminoglycoside attains a peak concentration of at least 4 mg/l and is maintained at a concentration of up to 4 mg/l for at least 1 hour thereafter.

In one embodiment, the sustained-release formulation further comprises hydropropylmethyl cellulose, other polymer matrices, gels, permeable membranes, osmotic systems, multilayer coatings, microparticles, liposomes, microspheres, or the like, or a combination thereof.

In a third aspect, the invention provides a method of treating a microbial infection, comprising the step of administering to a subject in need thereof an antibacterial agent active on bacterial cell wall together with an aminoglycoside wherein the aminoglycoside attains a peak concentration of at least 4 mg/l which is maintained at a concentration of up to 4 mg/l for at least 1 hour; wherein said aminoglycoside potentiates the activity of said antibacterial agent.

Preferably, the antibacterial agent is active on bacterial cell wall and acts at or near the cell wall of the bacteria. More preferably, the antibacterial agent is a β-lactam. Even more preferably the antibacterial agent is selected from the group consisting of cephalosporin, cephalothin, cephaloridine, cephalexin, cephaglycin, cephradine, cefaclor, cefoxitin, cefamandole, cefotaxime, ceftriaxone, ceftazidime, cefotetan, cephalosporin, cephamycin, penicillin G, ampicillin, methicillin, flucloxacillin, carbenicillin, ticarcillin, piperacillin, or imipenin. Most preferably, the antibacterial agent is cephazolin.

The aminoglycoside is most preferably gentamicin or tobramycin.

In a preferred embodiment, the activity of cephalosporin is potentiated by administering to a subject an amount of gentamicin or tobramycin effective to produce a peak concentration of up to 18 mg/l plasma. This may be achieved by administration of 70–280 mg (1–4 mg/kg body weight) over 1–2 hours. Thereafter, the aminoglycoside is administered preferably at 5–20 mg/hr for 4–12 hours to maintain a plasma concentration of 1–4 mg/l. The aminoglycoside may further be maintained at a concentration of 1.0 mg/l plasma or less up to 24 hours.

Desirably, 300 mg of cephazolin as a specific example is administered over 24 hours, maintaining a plasma concentration at 2 mg/ml or more.

In a particularly preferred embodiment, the cell wall active antibacterial agent is at 2 mg/ml when the aminoglycoside is maintained at 1–4 mg/l, and for a further 8–24 hours thereafter.

The compositions of the invention may comprise a cephalosporin and an aminoglycoside in dosage-unit form and optionally, in admixture with a conventional, pharmaceutically acceptable carrier suitable for administration to a clinical or home patient by intramuscular, subcutaneous, intravenous, oral or rectal administration.

Preferably, the compositions of the invention would allow once-a-day administration of antibiotics either in hospital or at home.

Preferably, the aminoglycoside is selected from the group consisting of gentamicin, tobramycin, netilimicin, amikacin, kanamycin, neomycin and streptomycin or combinations thereof.

The method and composition of the invention may be used in the treatment of microbial infections caused by Gram-negative or Gram-positive bacteria and mycobacteria. Other conditions include but are not limited to surgical chemoprophylaxis, and focal or systemic sepsis.

The bacterial infection includes infections caused by a wide variety of Gram-positive and Gram-negative organisms with a variety of growth circumstances and requirements ranging from aerobic to anaerobic growth, including:

(a) Gram-positive bacteria such as *Strep.pyogenes* (Group A), *Strep.pneumoniae*, *Strep*.GpB, *Strep.viridans*, *Strep*.GpD-(Enterococcus), *Strep*.GpC and GpG, *Staph.aureus, Staph.epidermidis, Listeria monocytogenes, Anaerobic cocci, Clostridium* spp., and *Actinomyces* spp; and (b) Gram-negative bacteria such as *Escherichia coli, Enterobacter aerogenes, Klebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Shigella* spp., *Yersinia enterocolitica, Acinetobacter calcoaceticus, Flavobacterium* spp., *Haemophilus influenzae, Pseudomonas aueroginosa, Campylobacter jejuni, Vibrio parahaemolyticus, Brucella* spp., *Neisseria meningitidis, Neisseria gonorrhoea, Bacteroides fragilis*, and *Fusobacterium* spp.

as well as other organisms such as *Mycobacterium tuberculosis, Mycobaterium smegmatis* and other *Mycobacteria*.

Furthermore, selected antibacterial agent combinations may be used in accordance with the invention in the following clinical conditions:

(a) Surgical chemoprophylaxis such as: ear, nose and throat surgery (otolaryngology); genitourinary surgery; contaminated penetrating injuries of the skin; compound fractures; bite wounds; penetrating eye injuries; abdominal surgery; acute cholecystitis; perforated viscus; peritonitis with cirrhosis; and dental chemoprophylaxis; and (b) Focal and systemic sepsis such as: bacterial endocarditis; empirical therapy of systemic sepsis; skin cellulitis;

decubitis, ischaemic and diabetic ulcers; severe or hospital-acquired, or institutional pneumonia; urinary infection; febrile neutropaenia; prostatitis; epididymo-orchitis; suppurative wound infections; gangrene; osteomyelitis; and pulmonary tuberculosis (for streptomycin combinations according to the infection).

BRIEF DESCRIPTION OF THE FIGURES

FIG. 5a shows kill and regrowth patterns during control (antibiotic free) exposures (x), exposure to a constant 4 mg/l concentration of cephazolin alone ( ), exposure to a bolus profile of gentamicin with a 6 mg/l peak at 30 min, alone ( ), and combined exposure to the cephazolin and gentamicin profiles ( ).

FIG. 5b shows the comparable experiment when flucloxacillin exposure at a constant concentration of 2 mg/l substituted for cephazolin in the design.

DETAILED DESCRIPTION OF THE INVENTION

Figure 1A:
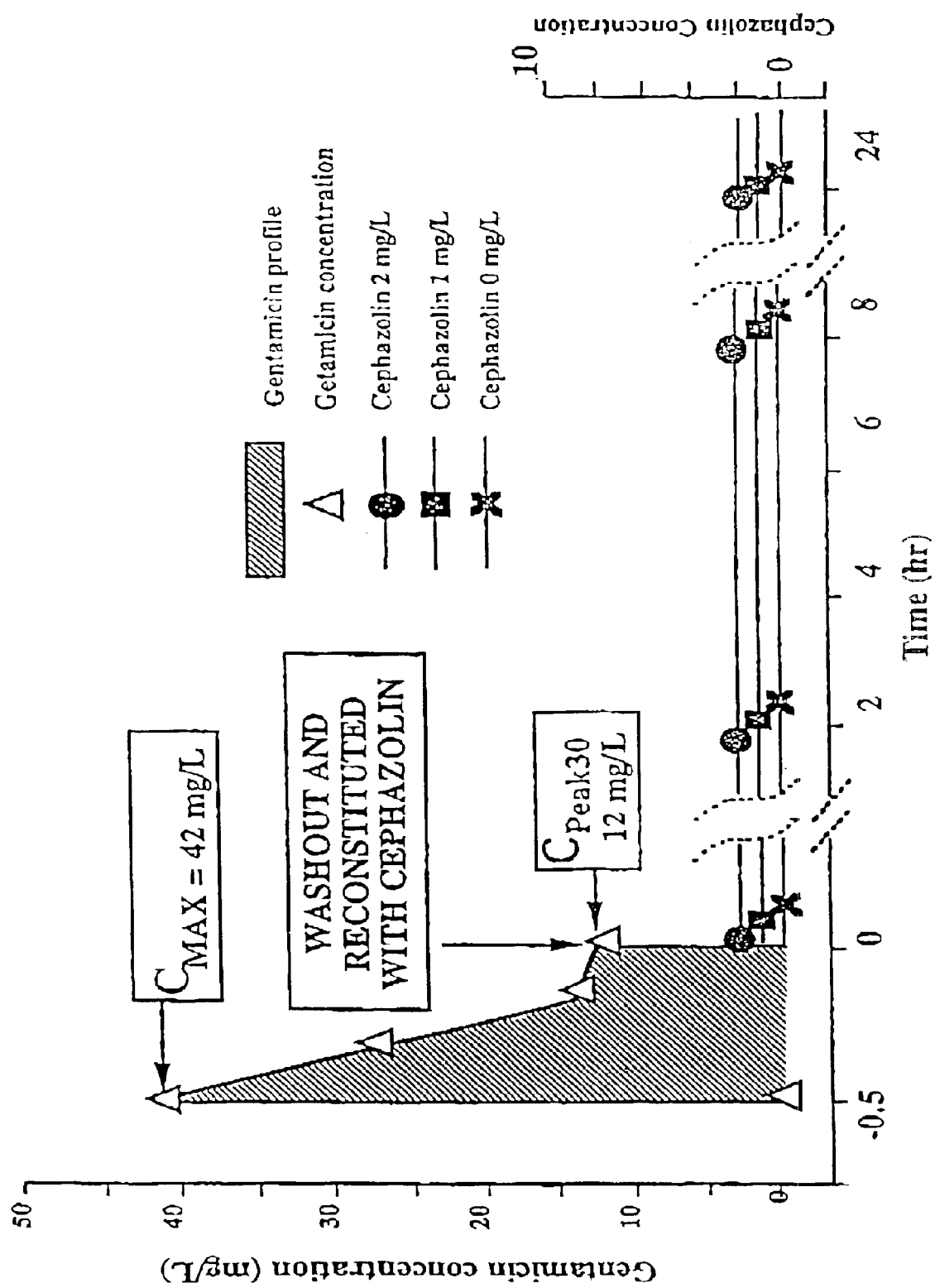
FIG. 1 shows the time-concentration profile of gentamicin after exposure of a culture of E. coli to a bolus of the aminoglycoside (IA) and the antibacterial action of a constant amount of different levels of cephazolin added 30 minutes after the bolus and removal of the gentamicin by centrifugation of culture medium at Time=0 (1B).

The method of the invention thus provides a critical profile of aminoglycoside exposure in the animal or human body which is necessary for optimisation of the action of aminoglycoside(s), but more particularly, for the potentiation of one or more other antibacterial agents. This also allows the avoidance and/or minimisation of the known clinical toxic effects of aminoglycosides on hearing, posture and dynamic balance. The profile is achieved by taking account of transfer of antibacterial agents from blood to tissues. However, provision is made in the method such that the antibacterial agent concentrations in the inner ear (vestibular apparatus and organ of Corti) do not achieve concentrations known to be toxic, and to prevent those toxic concentrations from being present for periods of time known to be necessary for toxic effects to develop. (McLean A. J., Ioannides-Demos L. L, Spicer W. J., Christophidis N, "Aminoglycoside dosing: one, two or three times a day?", Med J. Aust. 164:39–42, 1996).

As described above the antibacterial agent preferably a β-lactam such as cephazolin. The invention further contemplates other antibacterial agents. For example, agents directly related to cephazolin and sharing the potentiating mechanisms directly are cephalosporins and cephamycins, as exemplified by but not limited to the following: cephalosporin, cephalothin, cephaloridine, cephalexin, cephaglycin, cephradine, cefaclor, cefoxitin, cefamandole, cefotaxime, ceftriaxone, ceftazidime and cefotetan.

The cephalosporin dosage required for this invention is far lower than has been used before, specifically 0.166–0.33 g versus 1 g current minimum standard dose (Cahn M M et al, "Comparative serum levels and urinary recovery of cephazolin, cephalosporin and cephalothin in human", J. Clin. Pharmacol. 14:61–66, 1974).

Agents known generically as β-lactam antibiotics share mechanisms with cephazolin, and constitute the various penicillin groups and monobactams. Examples include the following: penicillin G, ampicillin, methicillin, flucloxacillin, carbenicillin, ticarcillin, piperacillin, imipenin.

Other agents which will benefit because of improved access to sites of action include diverse agents exemplified by: bacitracin, chloramphenicol, macrolides such as erythromycin, clarithromycin, rifampicin, vancomycin, quinolonem antibiotics such as nalidixic acid, norfloxacin, cycloserine and metronidazole.

The method utilises the property of aminoglycosides such as gentamicin. The peak concentrations of aminoglycoside which are most desirable are 4–18 mg/l, and are preferably maintained at a minimum of 1–4 mg/l, depending on bacterial sensitivity as evidenced by MIC testing. Maintenance of this level would require a mass of some 5–15 mg per hour of gentamicin to be delivered to the circulation of an average patient at a uniform rate, although variations will be required as a result of differing body size, renal function and various disease conditions (McLean et al 1996, supra). The rate and amount of active agent to be delivered can be determined easily by a person skilled in the art.

In accordance with existing formulation protocols, such exposure would presuppose intramuscular administration of a mixture of depot formulation. However, recent developments would allow for intravenous or oral formulations. Such formulations would need to deliver initial profiles as described above (4–18 mg/l), then allow for maintenance of concentrations at 1–4 mg/l for specific periods of time. Following this, lower levels of aminoglycoside and cephalosporin may be maintained for about 8 hours onwards. In one specific embodiment of the formulation, ongoing concentrations of aminoglycoside in the circulation should not exceed about 1 mg/l at about 8–16 hours after administration of the formulation, so as to prevent toxic levels of aminoglycoside accumulating in the inner ear and kidney.

The method of the invention also allows the effective dose of the antibacterial agent which is potentiated to be reduced. This again allows toxic effects to be negated or avoided.

The method of the invention allows the development of a pharmaceutical formulation of cephalosporins such as cephazolin which are clinically effective at ⅙ to ⅓ of the current clinical doses. Physical tolerance would be enhanced markedly so that intramuscular formulations can be realistically used and tolerated. However, advances in formulation should allow the development of intravenous or oral formulations to deliver greatly reduced concentrations of the drug required as a result of the aminoglycoside potentiation.

For example, sustained and/or timed release formulations may be made by sustained release means or delivery devices that are well known to those of ordinary skill in the art, such as those described in U.S. Pat. Nos. 3,845,770, 3,916,899, 3,536,809, 3,598,123, 4,008,719, 4,710,384, 5,674,533, 5,059,595, 5,591,767, 5,120,548, 5,073,543, 5,639,476, 5,354,556, and 5,733,566, the disclosures of which are each incorporated herein by reference. These pharmaceutical compositions can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

In a highly preferred embodiment, the sustained release formulation contains active ingredients such as, but not limited to, microcrystalline cellulose, maltodextrine, ethylcellulose, and magnesium stearate. In yet another highly preferred embodiment, the formulation is synthesized with a CapsuDar(R) SR (Biodar, Yavne, Israel) microencapsulation which consists of the active ingredients microcrystalline cellulose, maltodextrine, ethylcellulose, and magnesium stearate.

As described above, all known methods for encapsulation which are compatible with the properties of aminoglycosides and antibacterial agents are encompassed by this invention. The sustained release formulation is encapsulated by coating particles or granules of the pharmaceutical composition of the invention with varying thicknesses of slowly soluble polymers or by microencapsulation. In a preferred embodiment, the sustained release formulation is encapsulated with a coating material of varying thickness (e.g., about 1 micron to 200 microns) that allows the dissolution of the pharmaceutical composition about 48 hours to about 72 hours after administration to a mammal. In another embodiment, the coating material is a food approved additive. In yet another embodiment, the coating material is sold under the trademark Eudragit RS or RL (Rohm Pharma, Germany).

In another embodiment, the sustained release formulation is a matrix dissolution device, which is prepared by compressing the aminoglycoside and antibacterial agent with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, have a relatively high percentage of plasticizer in the coating in order to permit sufficient flexibility to prevent substantial breakage during compression. The specific amount of plasticizer varies depending on the nature of the coating and the particular plasticizer used. The amount may be readily determined empirically by testing the release characteristics of the tablets formed. If the medicament is being released too quickly, then more plasticizer is used. Release characteristics are also a function of the thickness of the coating. When substantial amounts of plasticizer are used, the sustained released capacity of the coating diminishes. Thus, the thickness of the coating may be increased slightly to make up for an increase in the amount of plasticizer. Generally, the plasticizer in such an embodiment will be present in an amount of about 15 to 30 percent of the sustained release material in the coating, preferably 20 to 25 percent and the amount of coating will be from 10 to 25 percent of the weight of active material, preferably 15 to 20 percent. Any conventional pharmaceutically acceptable plasticizer may be incorporated into the coating.

The aminoglycoside and antibacterial agent of the invention are formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: (1) extended activity of the composition; (2) reduced dosage frequency; and (3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the aminoglycoside that promptly produces the desired effect, namely 4–14 mg/l and gradually and continually release of other amounts of aminoglycoside to maintain a level of up to 4 mg/l for at least one hour. In order to maintain this constant level in the body, the aminoglycoside must be released from the dosage form at a rate that will replace the aminoglycoside being metabolized and excreted from the body.

The sustained release of the aminoglycoside may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the sustained release formulation is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol.

In a further aspect, the invention involves the administration in specified ways of an aminoglycoside(s) to optimise the action of the aminoglycoside alone and to potentiate the action of one or more antibiotic agents which act at or near cell wall sites of bacterial cells.

When cephalosporins are placed in culture medium containing susceptible bacteria, cephalosporin diffuses down the concentration gradient existing between the concentration in the culture medium and the concentration at the sites of action on the bacterial cell wall. The action of cephalosporinases chemically degrades and inactivates the cephalosporin such that there are limitations on the degree of inhibition of growth of the bacteria.

Figure 1B:
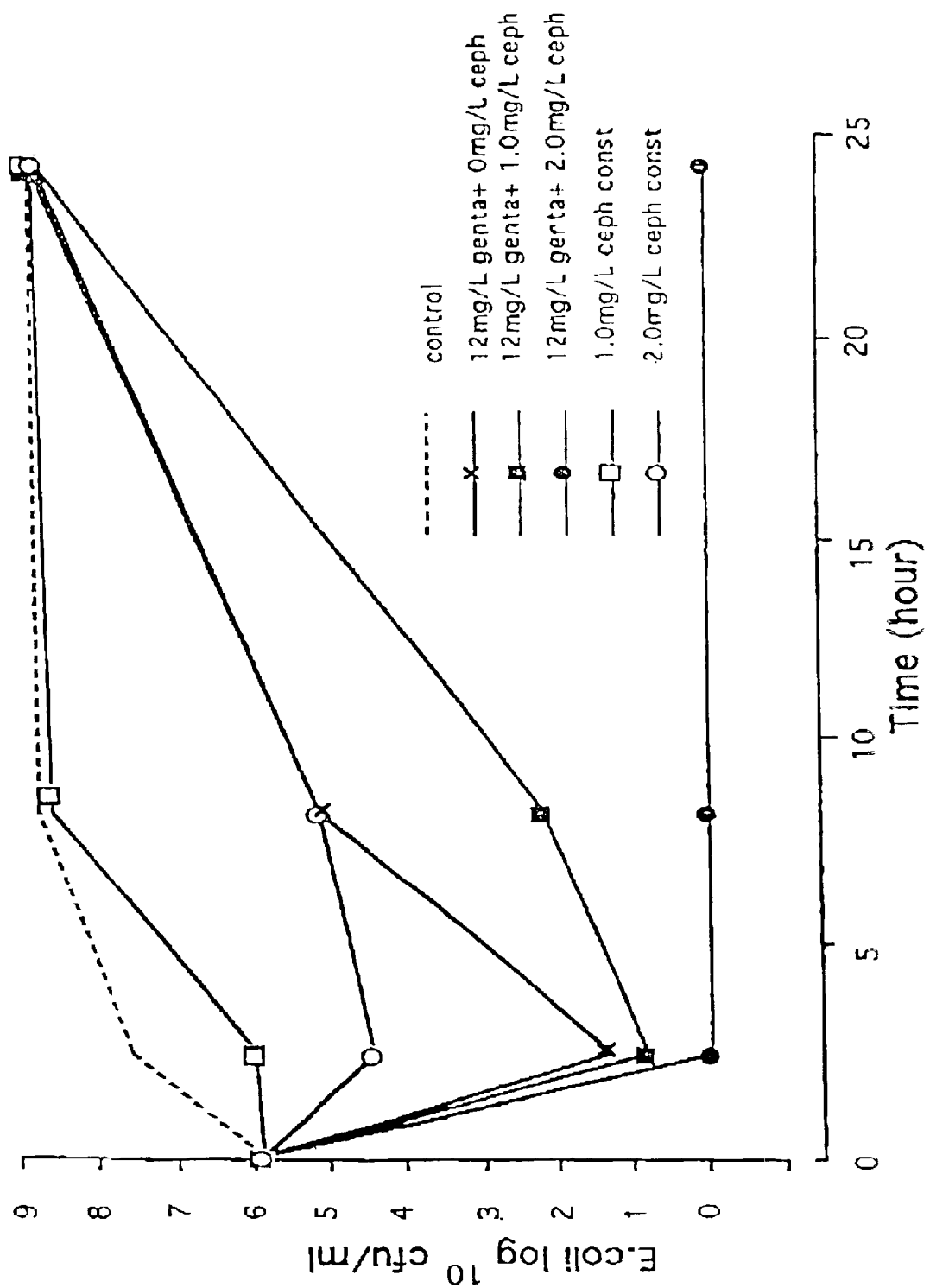
Figure 2A:
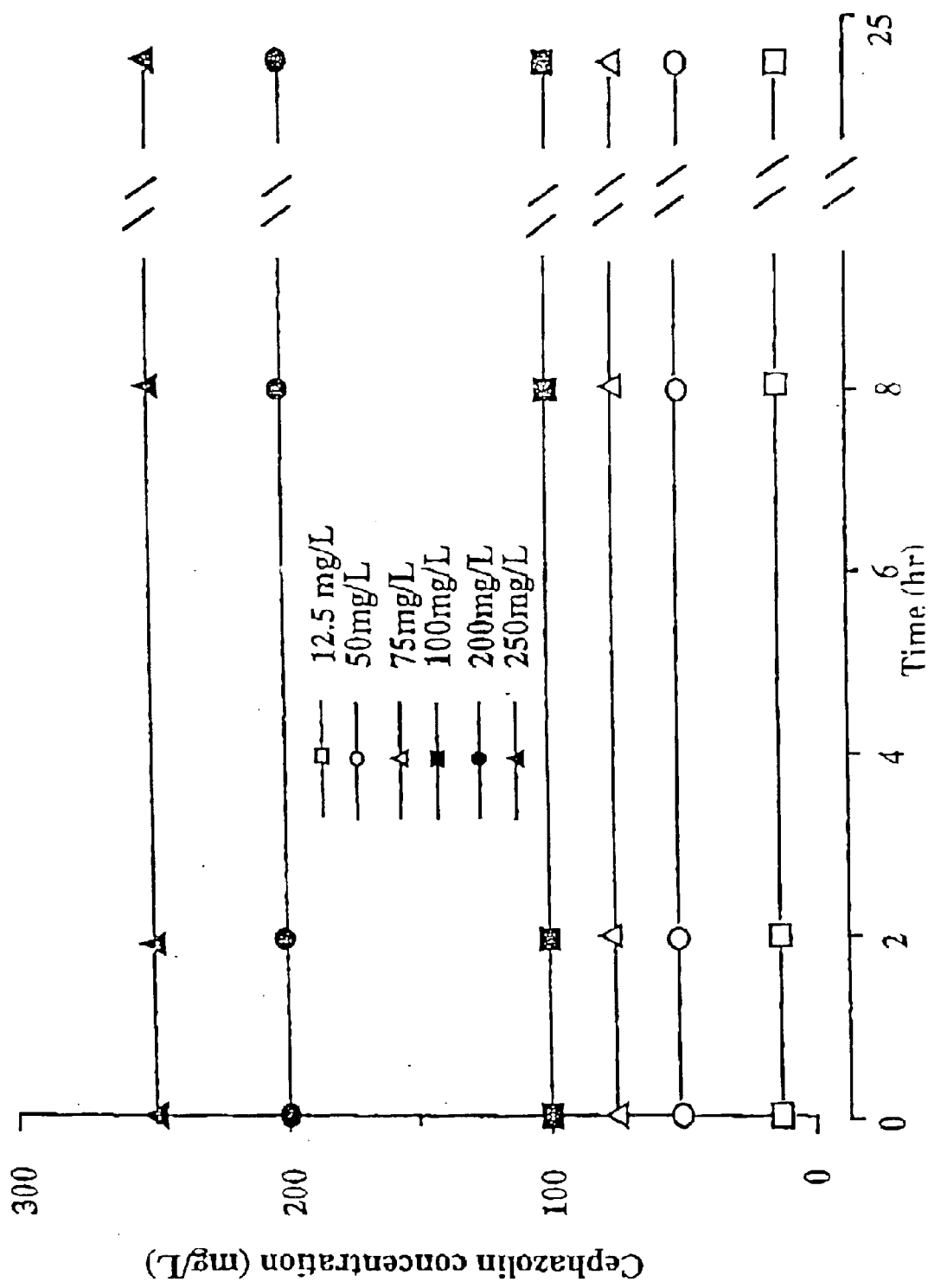
FIG. 2 shows the antibacterial action of cephazolin on E. coli (2B) following exposure of colonies to different concentrations of the antibacterial agent (2A).
Figure 2B:
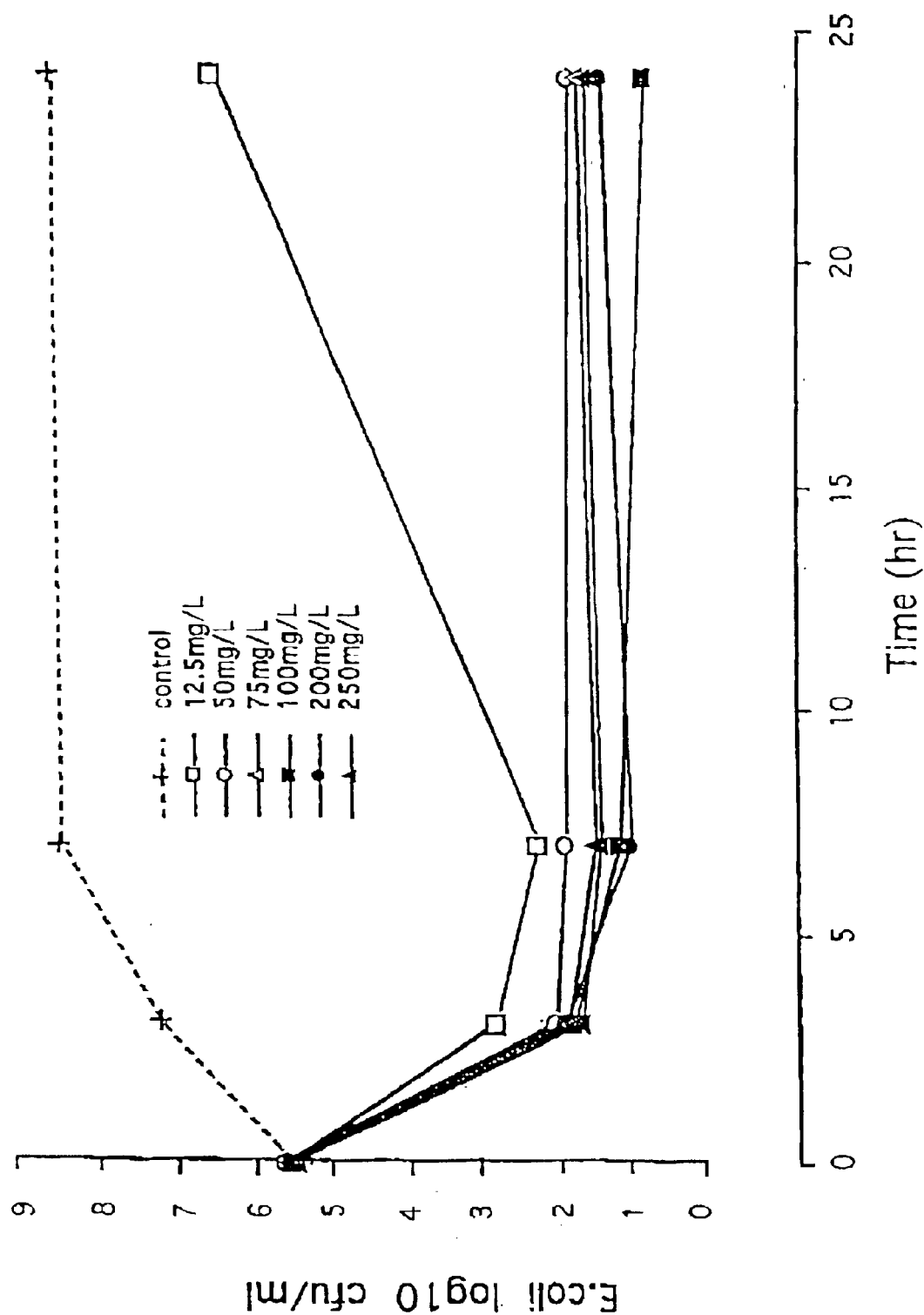
Figure 3A:
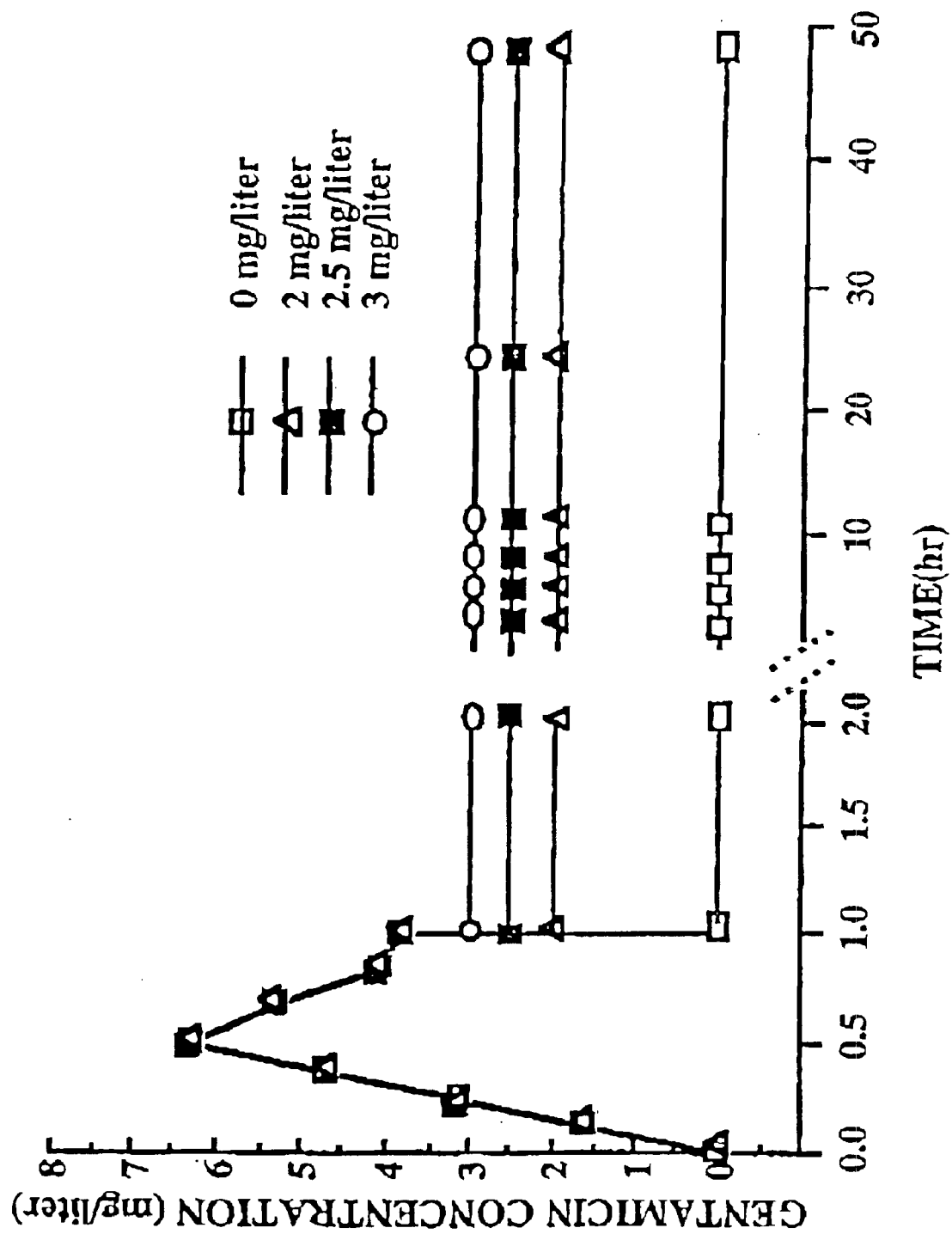
FIG. 3 shows the time-concentration profile of gentamicin (3A) and E. coli counts (3B) following exposure to the aminoglycoside. The aminoglycoside reached a peak concentration of 4 mg/l 30 minutes post-dose and was removed from the E. coli culture by washing. Medium containing 0, 2, 2.5 and 3 mg/l gentamicin was reconstituted and added to the culture at 1 hour after initial exposure to the aminoglycoside (n=6).
Figure 3B:
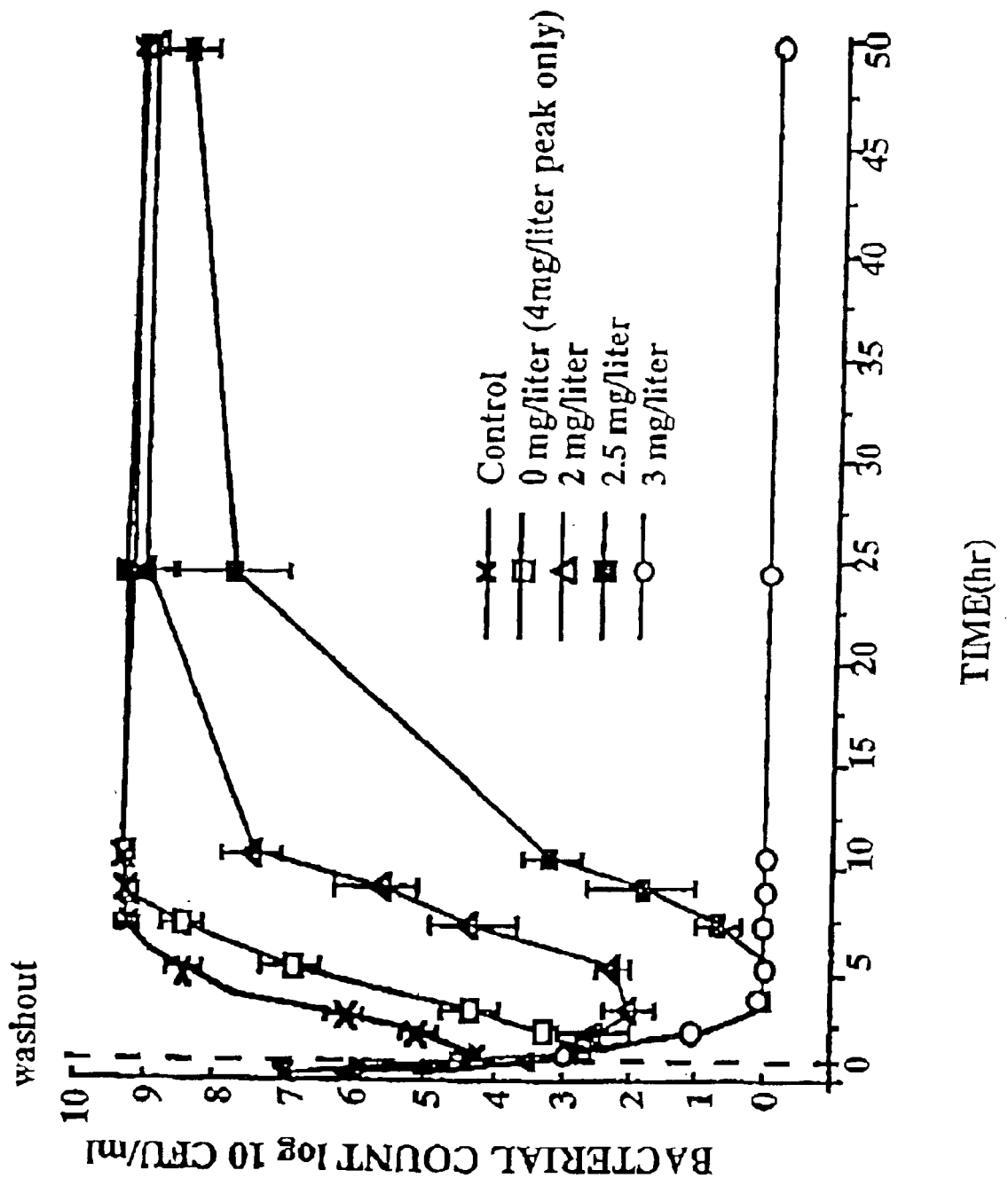

In comparative experiments described in the examples herein, a reference strain of *Escherichi coli* (*E. coli* NCTC 10418) was exposed to constant concentrations of cephazolin in the culture medium (see FIGS. 1A and IIA). As these concentrations were varied, the growth of the bacterial culture was changed. At the lowest concentration of cephazolin (1.0 mg/l) the growth of the culture was delayed in relation to control (see FIG. 1B). As concentrations in the medium were increased, there was a major decline in numbers and a delay in regrowth.

However, it was not possible to produce a complete kill or eradication of E. coli NCTC 10418 using cephalosporin alone. The organisms in the media were able to maintain their numbers in a reduced state even in the continuing presence of cephazolin. This outcome is due to the exclusion of cephalosporins by porin channels in the outer cell wall and to the action of cephalosporinase which keeps cephazolin levels at the site(s) of action below that required for full bactericidal effect.

When a blood culture isolate of cMRSA was exposed to gentamicin, cephazolin or flucloxacillin, complete kill or eradication was not achieved. Complete bactericidal effect was evident at 4.5 hours when the bacterial isolate was exposed to a bolus profile of gentamicin with a target peak of $C_{peak30}$ 6 mg/l (see FIG. 1) and 4 mg/l of cephazolin (see FIG. 5(a)). Similarly complete kill was achieved with the combination of this bolus profile of gentamicin and a constant 2 mg/l concentration of flucloxacillin (See FIG. 5(b)).

For oral administration, the sustained release formulation may be in liquid form, (e.g., solutions, syrups or suspensions), or may be presented as a drug product (e.g., capsule or powder) for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. In a preferred embodiment, the pharmaceutical composition may take the form of a capsule or powder to be dissolved in a liquid for oral consumption.

Preparations for oral administration may be suitably formulated to give controlled release of the active compound. In a preferred embodiment, the compounds of the present invention are formulated as controlled release powders of discrete micro-particles which can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in U.S. Pat. No. 5,354,556 which is incorporated by reference in its entirety. Particularly suitable polymers include those described, but not limited to, those described in U.S. Pat. No. 5,354,556 which is incorporated by reference in its entirety.

For buccal administration, the compositions may take the form of tablets or lozenges formulated in conventional manner.

The sustained release compounds of the invention may be formulated for parenteral administration, e.g., by intramuscular injections or implants for subcutaneous tissues and various body cavities and transdermal devices.

Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In a preferred embodiment, intramuscular injections are formulated as aqueous or oil suspensions. In an aqueous suspension, the sustained release effect is due to, in part, a reduction in solubility of the aminoglycoside and antibiotic upon complexation or a decrease in dissolution rate. A similar approach is taken with oil solutions and suspensions, wherein the release rate of the aminoglycoside and antibiotic are determined by partitioning of the aminoglycoside or antibiotic out of the oil into the surrounding aqueous medium. Only aminoglycosides or antibiotics which are oil soluble and have the desired partition characteristics are suitable. Oils that may be used for intramuscular injection include, but are not limited to, sesame, olive, arachnis, maize, almond, cottonseed, and castor oil.

A highly developed form of drug delivery that imparts sustained release is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

The aminoglycoside/antibacterial agent sustained release formulation may also be formulated in rectal compositions such as suppositories or retention enemas, e.g., containing conventional suppository bases such as cocoa butter or other glycerides.

The aminoglycoside/antibacterial agent sustained release formulation may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers having therapeutically or prophylactically effective amounts of the aminoglycoside/ antibacterial agent sustained release formulation in pharmaceutically acceptable form. The sustained release formulation of the invention may be in the form of a pharmaceutically acceptable solution, e.g., in combination with sterile saline, dextrose solution, or buffered solution, or other pharmaceutically acceptable sterile fluid contained within a vial. Alternatively, the formulation may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of the aminoglycoside/antibiotic formulation by a clinician or by the patient.

The invention will now be described in detail by way of reference only to the following non-limiting examples, and to the figures.

While a representative microorganisms, *E. coli.* and methicillin resistant *Staphylococcus aureus*, a representative aminoglycoside antibiotic (gentamicin) and a representative cephalosporin (cephazolin) were studied herein to generate the majority of data presented, it will be clearly understood that the invention is not limited to this microorganism or to these specific agents.

EXAMPLE 1

Antibacterial Action of Aminoglycoside and Cephalosporin on *E. coli* Cultures The experimental work described herein involved testing bacterial response while changing aminoglycoside concentrations with time in the test tube, and mimics closely measurements made in man under clinical conditions (Bastone E B, Li S C, Ioannides-Demos L L, Spicer J., McLean A J, "Kill kinetics and regrowth patterns of *E. coli* exposed to gentamicin concentration-time profiles simulating in vivo bolus or infusion dosing", Antimicrob Agents Chemother. 37:914–917, 1993).

With each antibiotic, concentration-time profiles similar to those observed in the blood of clinical patients following conventional intravenous dosing of an aminoglycoside (gentamicin) and pump-driven profiles of gentamicin and cephalosporin (cephazolin) were attained. The concentration-time profiles for each drug class have the general form shown in FIG. IA and FIG. IIIA of the accompanying drawings. Additionally a gentamicin profile of the form shown in FIG. IIIA was generated, which reached a peak of 12 mg/l over 3 hours, was maintained at 12 mg/l for a further hour, then was reconstituted to a range of steady-state concentrations (0, 0.5, 1.0, 2.0, 3.0, 4.0 mg/l) to yield the experimental results shown in Table 4.

As shown FIG. IA, the pre-exposure to gentamicin provides a model of an in vivo bolus which generates a transient peak (C max) of 42 mg/L followed by a decrease over 30 minutes to 12 mg/L (C peak 30). The form of this profile is governed in vivo by distribution into tissue from the central circulation. In in vitro experiments, gentamicin was removed (T=0 time) by centrifugation and washing with antibiotic-free medium. The incubation was reconstituted with media containing 0 mg/l, 1 mg/l or 2 mg/l cephazolin (see FIG. IA).

The quantitative influence of antibiotic exposure on bacterial growth is detailed in Table 1, and illustrated diagrammatically in FIG. IB. The figure shows the number of colonies of *E. coli* which grew on microbiological culture plates when samples of the broth culture were taken at standard times throughout the antibiotic exposure regimens (FIG. IA).

In FIG. IB, it can be seen that the pattern of growth of control organisms (not exposed to antibiotic) is designated by the dotted line ( - - - ), while the growth patterns of test organisms are represented by the solid lines with symbols indicating each type of treatment or test (FIG. IB). Colony numbers declined initially to 2 h (due to bactericidal effect), then a variable pattern and degree of recovery followed. The treatment with gentamicin alone, or combined with cephalosporin, resulted in the greatest decline in numbers and slow or no recovery. Pretreatment with gentamicin (C peak 30=12 mg/l) followed by maintained concentrations of 2.0 mg/l cephazolin (see FIG. 1A) resulted in complete kill (see FIG. IB) or eradication of the *E. coli.*

These results are in marked contrast to the findings with exposures to constant concentrations of cephalosporin alone (FIG. IIA), tested over a very wide range of levels up to 250 mg/l (see FIG. IIA). The cephalosporin effect reached a maximum when *E. coli* growth was reduced to 10 colony forming units(cfu)/ml (see FIG. IIB).

The data reflect an approximately 200-fold increase in the activity of standard cephalosporins as a result of administration or exposure of this antibiotic in a specific manner i.e. constant concentrations for lengths of time in combination with highly specific and novel profiles of gentamicin.

Without wishing to be bound by any proposed mechanism for the observed advantages of the invention, the novel action of aminoglycoside reported herein can be explained by at least two possible underlying mechanisms of action. The first possibility is the creation of new channels in the external membrane(s) allowing facilitated access of cephalosporin to the sites of cephalosporin action, such new channels resulting in reduced exposure of the cephalosporin to cephalosporinases. The alternative explanation, considered to be less likely, is that the profile of aminoglycoside exposure in terms of both concentration and time results from direct inhibition of the cephalosporinases present in the normal porin pathways and located at or near the cephalosporin binding sites, thus resulting in potentiation of the action of cephalosporin.

It is believed that cephalosporins act on the structural cell wall and create "holes" for entry of agents such as aminoglycosides which act inside the cell. In contrast, aminoglycosides are believed to make initial minor breaches across the outer wall, then pass through these breaches, cross the inner wall and cell membrane to act predominantly intracellularly on 30S ribosomes and related structures within the cell and thus inhibit general cell metabolism, including cell wall synthesis. Despite indications of a surface cell wall action, it has been and currently is generally accepted that the major action of aminoglycosides is inside the cell.

A capacity for an aminoglycoside to facilitate access of a cephalosporin to its surface site of action is evidenced by the potentiation of the effect of cephazolin as reported herein. The invention therefore contemplates administration of a combination of an aminoglycoside and a surface-acting antimicrobial (e.g. cephalosporin).

Regardless of the exact mechanism which might be finally determined, the observations allow radical redesign of aminoglycoside and cephalosporin formulations either alone or as combination formulations. The aminoglycoside profile will be one of two types, depending on the clinical circumstances. When the setting is of serious illness and the therapeutically targeted organisms are in the blood-stream, the aminoglycoside profile indicated is shown in FIG. IA. In contrast, where the infection is tissue based, the exposure required is a maintained profile of aminoglycoside as illustrated in FIG. IIIA.

For aminoglycosides, totally novel information is also represented by the data in Table 3 and Table 4. The studies here revealed both a desirable concentration requirement (in this case a peak requirement of 4–12 mg/l and a maintained concentration requirement of 1.0–4.0 mg/l) and a particularly preferred time requirement of 4–8 hours. This group of data together produce a paradigm shift in response pattern compared to lower concentrations e.g. 2.5 mg/l (see FIG. IIIB and Bastone et al, 1993, supra).

Figure 4:
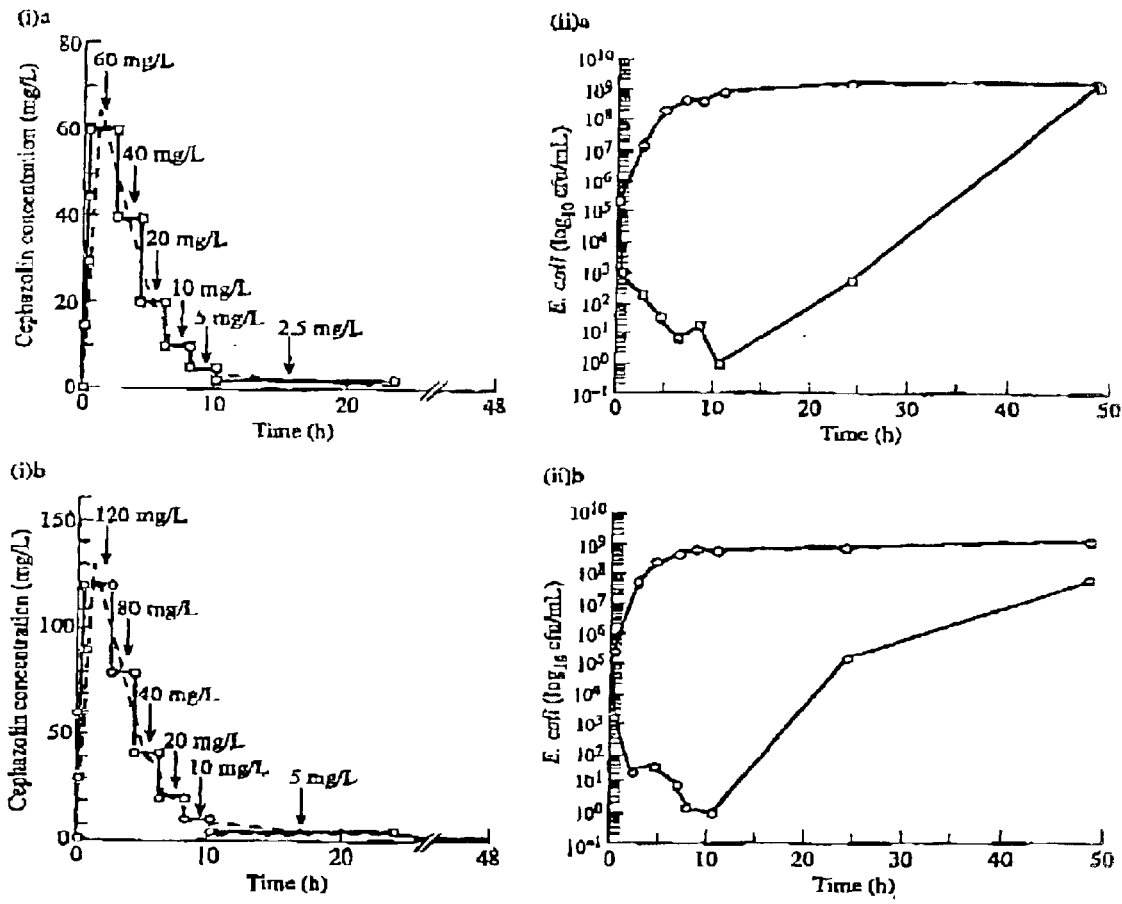
FIG. 4 Cephazolin concentration-time profiles under in-vitro conditions (i)a and kill kinetics and regrowth patterns of E coli following a cephazolin 1 g intramuscular profile (ii)a. A control profile (antibiotic free) was also run in parallel. For all studies n=6.

The cephalosporin profile is preferably a constant concentration of 2 mg/l or above, depending on the relative resistance of the target pathogen to the combination of aminoglycoside/cephalosporin. In the most serious infections, a maximum concentration of 60 mg/l of cephazolin is administered and maintained at this concentration for up to 2 hours, decrementing over a 10 hour period and further maintained at around 2 mg/l (See FIG. 4). The type of formulation which could be applied in the first instance is that normally used for intramuscular administration of cephalosporin. When the circulation is compromised due to serious infection, intravenous formulation could be used. Formulations for intravenous or oral use can be developed by a person skilled in the art without difficulty with the aim of maintaining the required minimum concentrations.

The time boundaries for maintained exposures with aminoglycoside may be 1.0–16 hours, while the required maintained concentrations will be a function of the resistance of the organism as determined by the minimum inhibitory concentration (MIC) of the pathogen isolated in culture and time-concentration requirements of the organism(s) being treated. For *E. coli* NCTC 10418 described herein, the maintained concentration/MIC ratio required for gentamicin was demonstrated to be 6:1, while the ratio for cephazolin (in the presence of gentamicin) was 2:1. In contrast, resistant Pseudomonas organisms required peak concentrations of 18 mg/l, while the ratio of maintained concentration: MIC was 0.5.

EXAMPLE 2

Effect of Tobramycin and Cephalosporin on Pseudomonas

The range of aminoglycoside antibiotics was extended to include tobramycin, the bacterial species type was extended from *Enterobacteriaceae* to *Pseudomonacea*, and the organism response range broadened to include an antibiotic resistant strain in *Pseudomonas* studies.

We have established the principles of the required degree and pattern of alteration in drug delivery requirement with variation in MIC from studies of a reference strain of *Pseudomonas aeruoginosa*, ATCC27853 (MIC=1 mg/l), and an antibiotic resistant strain of this organism (MIC=2–4 mg/l), isolated from a clinical patient.

The reference strain was killed by a tobramycin profile with initial patterns of the type shown in FIG. IIIA but with a concentration of 8 mg/l at 1 hour, reducing systematically until 8.5 hr when a fixed concentration of 0.8 mg/l for 16 hours resulted in complete kill. In contrast, the resistant clinical strain required a peak concentration of 18 mg/l combined with a maintained level of 1 mg/l.

EXAMPLE 3

Antibacterial Action of Gentamicin and Cephazolin on cMRSA Cultures

The CMRSA isolate was cultured in the presence of gentamicin (Delta West, Bentleigh, Australia). An overnight culture of cMRSA in brain heart infusion broth (BHIB) (Oxoid, Bainstoke, England) was diluted to $10^7$ CFU/ml in 0.1% peptone water (Oxoid, Bainstoke, England). A 1 ml sample of the $10^7$ CFU/ml culture was added to the experimental culture broth, resulting in an initial density of $10^6$ CFU/ml. In vitro concentration-time modeling of clinical plasma gentamicin concentration-time profiles assumed linear extrapolation of in vivo data as reported previously.[18] (Bastone et al Antimicrobial Agents and Chemotherapy 37(4): 914–917, 1993). The lowest-dose bolus profile included a $C_{max}$ of 17.5 mg/L, a postdistributional peak concentration of 5 mg/l and a half-life of decline of 2 hours. The equivalent infusion profile had a $C_{max}$ of 8.1 mg/l, a post-distributional peak concentration of 5 mg/l at 30 minutes and a half-life decline of 2 hours. Other profiles were constructed by linear extrapolation of these profiles and included 7 and 16 mg/l bolus and infusion profiles. Colony counts were performed at times 0, 0.5, 2.5, 4.5, 6.5, 8.5, 10.5, 24.5 and 48.5 hours for bolus profiles and times 0, 1, 3, 5, 7, 9, 11, 25 and 49 hours for infusion profiles. All results were compared with those [control] cultures not exposed to gentamicin.

In the experiments involving cephazolin the concentration was maintained at 4 mg/l in the BHIB for the entire 48.5 hours. For the experiments involving flucloxacillin the concentration of flucloxacillin was maintained at 2 mg/l for 48.5 hours. Colony counts were performed at times 0, 0,5, 2.5, 4.5, 6.5, 8.5, 10.5, 24.5 and 48.5 hours. All results were compared with those of control cultures. These included cMRSA in a drug free broth, cMRSA exposed to a bolus profile of gentamicin with a target $C_{peak\ 30}$ of 6 mg/l only, cMRSA exposed to 4 mg/l of flucloxacillin only.

All experiments involved six replicates. Gentamicin concentrations were measured at times 0, 0.16, 0.33, 0.5, 2.5, 4.5, 6.5, 8.5, 10.5, 24.5 and 48.5 hours. Gentamicin assay concentrations were determined by fluorescence polarisation immunoassay (AxSYM, Abbot, Ill., U.S.A.) which has a threshold for detection of 0.3 mg/liter. Assay results were linear over 0.3 to 10 mg/l ($r^2=0.99$). The interrun coefficient of variation was 6.0 to 16.3% over a range of 0.3 to 7 mg/l and the intrarun coefficient of variation was 9.9% at 0.3 mg/l, 7.4% a 3 mg/l and 3.8% at 7 mg/l. The AUC of gentamicin from 0 to 48.5 was calculated by using the trapezoidal rule. (Gibaldi et al, pharmaceutics $2^{nd}$ edn, 1982).

A blood culture insolate of cMRSA with the following characteristics was used for this study, mecA positive (the gene encoding for methicillin resistance), MIC 1 mg/l and MBC 4 mg/l for gentamicin, MIC 32 mg/l and MBC 32 mg/l of cephazolin, MIC 32 mg/l and MBC>32 mg/l of methicillin. The student test was used for statistical analysis with a significant level of 0.05, it was performed using the Sigma Stat 32 program (SPSS Inc 1992–1997).

The blood culture cMRSA isolate was exposed to gentamicin in vitro simulating an in vivo bolus dosing regimen with varying 30 minute post dose concentrations of gentamicin. The same organism was then exposed to gentamicin in vitro simulating an in vivo bolus dosing regime with a 30 minute post dose concentration of 6 mg/l and constant concentration of 4 mg/l of cephazolin or 2 mg/l of flucloxacillin for 48 hours.

Figure 5A:
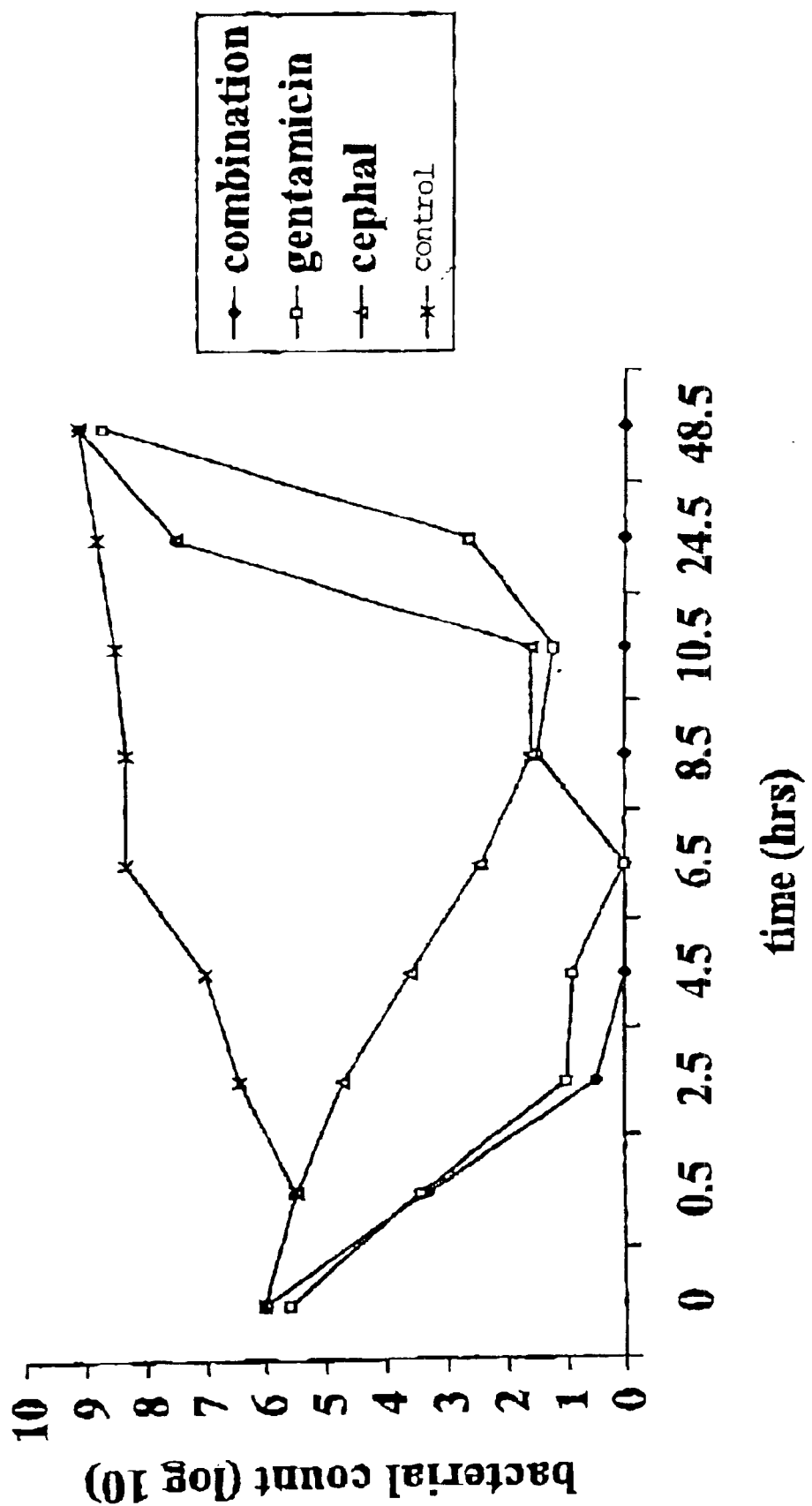
FIGS. 5a and 5b Kill kinetics and regrowth patterns of a clinical isolate of cMRSA.
Figure 5B:
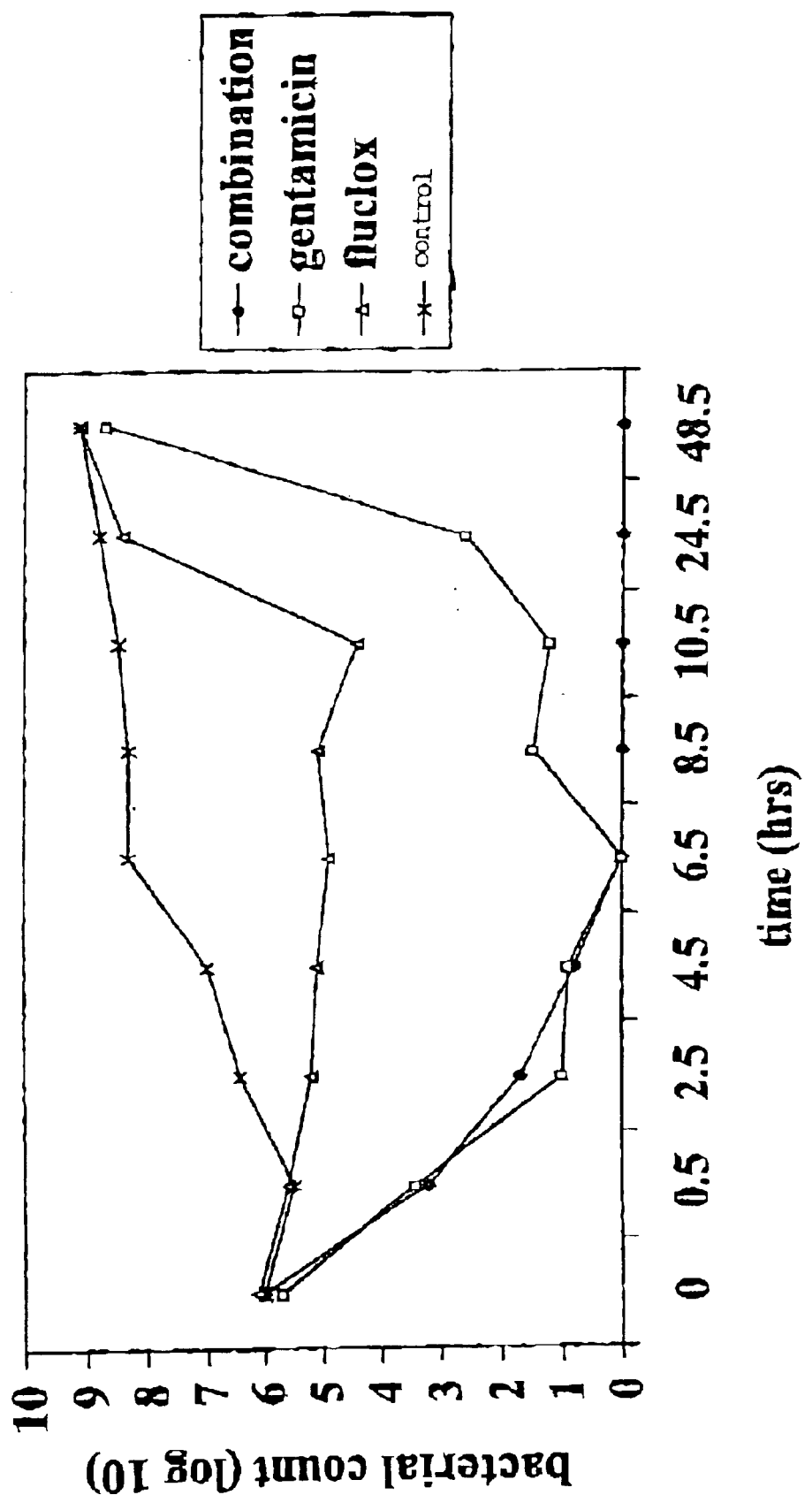

For all profiles bacterial growth in the absence of gentamicin showed a plateau at or near $10^9$ CFU/ml (See FIGS. 5a and 5b). Each of the profiles produced an early bactericidal effect followed by a bacteriostatic phase. For the bolus and infusion experiment profiles with a target $C_{peak30}$ of 7 mg/l of gentamicin the regrowth phase which began at 24.5 hours was dramatic and by 48.5 hours was close to those levels of the initial bacterial control. The infusion profile did show regrowth but well below that of the control. This pattern was the same with decreasing regrowth of the bolus profile, until that of a target $C_{peak30}$ of 16 mg/l when there was no regrowth in either of the profiles. The $C_{max}$ values between bolus and infusions were significantly different for all profiles. The AUCs for the bolus and infusion profiles with a target $C_{peak30}$ of 5 mg/l and 7 mg/l were not significantly different. However, the AUCs for the bolus and infusion profiles with a target $C_{peak30}$ of 16 mg/l were significantly different (P<0.001).

Bacteria in the presence of 4 mg/l of cephazolin alone throughout the experimental period displayed an early bactericidal effect evident by 2.5 hours (See FIG. 5(a)). This was followed by a bacteriostatic phase. Regrowth was evident at 24.5 hours and by 48.5 hours time bacterial numbers were close to those of the control culture. Bacteria exposed to a bolus profile with a target $C_{peak30}$ of 6 mg/l of gentamicin only showed an early bactericidal effect evident by 0.5 hours. This was however followed by a bacteriostatic phase and a recovery phase evident by 10.5 hours. Bacterial counts similar to those of the control were reached by 48.5 hours. Bacteria in the presence of a bolus profile of gentamicin with a target $C_{peak30}$ of 6 mg/l and 4 mg/l of cephazolin for the entire experimental period showed complete bactericidal effect evident by 4.5 hours.

Bacteria exposed to a bolus profile of gentamicin with a target $C_{peak30}$ of 6 mg/l and a constant level of 2 mg/l of flucloxacillin showed complete bactericidal effect evident by 6.5 hours ( FIG. 5b).

This study demonstrated that despite in vitro sensitivity, high doses of gentamicin were required to be effective against cMRSA. It was also demonstrated that as AUC increased, bactericidal effect also increased as the AUC was above the MIC for a longer period and the antibiotic concentration exceeded the MIC for increasing periods of time.

The combination of an aminoglycoside and a β-lactam were successful in killing cMRSA. Individually neither cephazolin or flucloxacillin were able to cause a bactericidal effect against cMRSA. When gentamicin was used alone then high levels were required.

Discussion and Conclusion

The synergistic nature of the combination of a β-lactam and an aminoglycoside represents a successful approach to treating cMRSA infections. The lower levels of gentamicin administered would allay most concerns about potential renal and auditory damage. A bolus method of administration also reduces concerns about toxicity as transiently elevated levels of aminoglycosides are less detrimental than constant exposure to these agents. Such a schedule would also allow for the concentration dependent bactericidal action, post antibiotic effect (PAE) and increased time for resolution of adaptive resistance to occur. The constant infusion of a β-lactam would provide time for these agents to have optimal effect, as their bactericidal activity is time dependent so their rate of kill may be maximised by such a protocol. There is also a suggestion that β-lactams may extend the PAE of aminoglycosides thereby increasing the antibacterial activity of aminoglycosides. This combination extends the usefulness of betalactams, decreasing the use of other antimicrobials (especially vancomycin) and therefore decreasing the chance of development of resistance to glycopeptide antibiotics.

Route of Administration

Intramuscular dosing is possible with the doses of cephalosporin and aminoglycoside contemplated by the invention because of the smaller volumes and hence better physical tolerance of the injection (currently a limiting factor). However, technological advances will allow formulations of both aminoglycoside and cephalosporin capable of providing the required profiles according to the invention to be generated by oral or intravenous dosing (Bakker-Woudenberg et al. J. Inf. Dis. 171: 938–947, 1995, Vincente et al, JAC 28: 269–271, 1990).

Other Embodiments of the Invention

In one embodiment, there is provided a method of using gentamicin or other aminoglycoside(s) in potentiating the action of a cephalosporin(s) or other antibacterial agent(s) acting at or near cell wall sites on pathogenic bacteria in the treatment of pathogenic bacterial infections in animals, particularly in the treatment of Gram-negative pathogenic bacterial infections in human patients, by administering to the animal or patient, either separately or together, the gentamicin or other aminoglycoside(s) and the cephalosporin(s) or other antibacterial agent(s) acting at or near cell wall sites on pathogenic bacteria, such that:

(i) the concentration of gentamicin or other aminoglycoside(s) in the animal or patient is maintained at a minimum of 1–4 mg/L for at least about 1 hour and preferably no more than about 16 hours, more preferably no more than about 12 hours, most preferably no more than about 4–8 hours, after the administration of the gentamicin or other aminoglycoside(s), but the concentration of gentamicin or other aminoglycoside(s) in the animal or patient recedes to 1 mg/L or less than 1 mg/l at about 16 hours, preferably at about 12 hours, more preferably at about 4–8 hours, after the administration of the gentamicin or other aminogylcoside(s); and (ii) the concentration of the cephalosporin(s) or other antibacterial agent(s) acting at or near cell wall sites on pathogenic bacteria in the animal or patient is maintained at about 2 mg/l when the concentration of the gentamicin or other aminoglycoside(s) is maintained at or above 1–4 mg/l; optionally, the concentration of the cephalosporin(s) or other antibacterial agent(s) acting at or near cell wall sites on pathogenic bacteria, being maintained at about 2 mg/L for a further period of time of at least about 8–24 hours after the concentration of gentamicin or other aminoglycoside(s) declines to a negligible level.

In another embodiment, a method of using gentamicin or other aminoglycoside(s) in potentiating the action of a cephalosporin(s) or other antibacterial agent(s) acting at or near cell wall sites on pathogenic bacteria in the treatment of pathogenic bacterial infections in animals, particularly in the treatment of Gram-negative and Gram-positive pathogenic bacterial infections in human patients is provided and comprises administering to the animal or patient, either separately or together, the gentamicin or other aminoglycoside(s) and the cephalosporin(s) or other antibacterial agent(s) acting at or near cell wall sites on pathogenic bacteria, such that:

(i) the concentration of gentamicin or other aminoglycoside(s) in the animal or patient is about 4–12 mg/L at about 30 minutes after the administration of the gentamicin or other aminoglycoside(s);

(ii) the concentration of gentamicin or other aminoglycoside(s) in the animal or patient is maintained at a minimum of 1–4 mg/l for at least about 1 hour and preferably no more than about the next 16 hours, more preferably no more than about the next 12 hours, most preferably no more than about the next 4–8 hours, after the administration of the gentamicin or other aminoglycoside(s), but the concentration of gentamicin or other aminoglycoside(s) in the animal or patient declines to 1 mg/l or less than 1 mg/l at about 16 hours, preferably at about 12 hours, more preferably at about 4–8 hours, after the administration of the gentamicin or other aminoglycoside(s); and (iii) the concentration of cephalosporin(s) or other antibacterial agents acting at or near cell wall sites on pathogenic bacteria, in the animal or patient is maintained at about 2 mg/l when the concentration of the gentamicin or other aminoglycoside(s) is maintained at or above 1–4 mg/l, optionally, the concentration of the cephalosporin(s) or other antibacterial agent(s) acting at or near cell wall sites on pathogenic bacteria, being maintained at about 2 mg/l for a further period of time of at least about 8–24 hours after the concentration of gentamicin or other aminoglycoside(s) declines to a negligible level.

A further embodiment of the present invention provides a composition suitable for the treatment of pathogenic bacterial infections in animals, particularly in the treatment of Gram-negative and Gram-positive pathogenic bacterial infections in human patients, comprising:

(a) a cephalosporin(s) or other antibacterial agent(s) acting at or near cell wall sites on pathogenic bacteria; and (b) a potentiating amount of gentamicin or other aminoglycoside(s), wherein the composition is formulated to deliver to the animal or patient: (i) the gentamicin or other aminoglycoside(s) at a maintained concentration of a minimum of 1–4 mg/l for at least about 1 hour and preferably for no more than about 16 hours, more preferably no more than about 12 hours, most preferably no more than about 4–8 hours, after the administration of the composition to the animal or patient, but the concentration of gentamicin or other aminoglycoside(s) in the animal or patient recedes to 1 mg/l or less than 1 mg/l at about 16 hours, preferably at about 12 hours, more preferably at about 4–8 hours, after the administration of the gentamicin or other aminoglycoside(s); and (ii) the cephalosporin(s) or other antibacterial agent(s) acting at or near cell wall sites on pathogenic bacteria, at a maintained concentration of about 2 mg/l when the concentration of the gentamicin or other aminoglycoside(s) is maintained at or above 1–4 mg/l, optionally, the composition further delivering to the animal or patient, the cephalosporin(s) or other antibacterial agent(s) acting at or near cell wall sites on pathogenic bacteria, at a maintained concentration of about 2 mg/l for a further period of time of at least about 8–24 hours after the concentration of gentamicin or other aminoglycoside(s) declines to a negligible level.

In yet another embodiment, the present invention provides a composition suitable for the treatment of pathogenic bacterial infections in animals, particularly in the treatment of Gram-negative and Gram-positive pathogenic bacterial infections in human patients, comprising:

(a) a cephalosporin(s) or other antibacterial agent(s) acting at or near cell wall sites on pathogenic bacteria; and (b) a potentiating amount of gentamicin or other aminoglycoside(s), wherein the composition is formulated to deliver to the animal or patient: (i) the gentamicin or other aminoglycoside(s) at a concentration of about 4–18 mg/l at about 30–240 minutes after the administration of the composition to the animal or patient; (ii) the gentamicin or other aminoglycoside(s) at a maintained concentration of a minimum of 1–4 mg/l for at least about 1 hour and preferably for no more than about 16 hours, more preferably no more than about 12 hours, most preferably no more than about 4–8 hours, after the administration of the composition to the animal or patient, but the concentration of gentamicin or other aminoglycoside(s) in the animal or patient recedes to 1 mg/l or less than 1 mg/l at about 16 hours, preferably at about 12 hours, more preferably at about 4–8 hours, after the administration of the gentamicin or other aminoglycoside(s); and (iii) the cephalosporin(s) or other antibacterial agent(s)acting at or near cell wall sites on pathogenic bacteria, at a maintained concentration of about 2 mg/l when the concentration of the gentamicin or other aminoglycoside(s) is maintained at or above 1–4 mg/l, optionally, the composition further delivering to the animal or patient, the cephalosporin(s) or other antibacterial agent(s) acting at or near cell wall sites on pathogenic bacteria, at a maintained concentration of about 2 mg/l for a further period of time of at least about 8–24 hours after the concentration of gentamicin or other aminoglycoside(s) declines to a negligible level.

Although the invention has been described in detail for the purposes of clarity and understanding, it will be apparent to the person skilled in the art that various modifications and/or additions may be incorporated in the invention without departing from the spirit and scope thereof as described.

References

1. O'Kane, G. M., Gottlieb, T. & Bradbury, R. (1998). Staphylococcal bacteraemia: the hospital or the Home? A review of Staphylococcus aureus bacteraemia at Concord Hospital in 1993. Australia and New Zealand Journal of Medicine. 28, 23–27.
2. Rosenberg, J. (1995). Methicillin-resistant Staphylococcus aureus (MRSA) in the community: who's watching? The Lancet, 346, 132–133.
3. Pate, K. R., Nolan, R. L., Bannerman, R. I. & Feldman, S. (1995). Methicillin-resistant Staphylococcus aureus in the community. The Lancet, 346, 978.
4. Boyce, J. M. (1998). Are the epidemiology and microbiology of methicillin-resistant Staphylococcus aureus changing? JAMA, 279(8),623–624.
5. Herold, B. C. Immergluck, L. C., Maranan, M. C., Lauderdale, D. S., Gaskin, R. E., Boyle-Vavra, S., Leitch, C. D. and Daum, R. S. (1998). Community-acquired methicillin-resistant Staphylococcus aureus in children with no identified predisposing risk. Journal of the American Medical Association, 279(8), 593–598.
6. Lindenmayer, J. M., Schoenfeld, S. O'Grady, R. and Carney, J. K. (1998). Methicillin-resistant Staphylococcus aureus in a high school wrestling team and the surrounding community. Archives of Internal Medicine, 158, 895–899.
7. Moreno, F., Crisp, C., Jorgensen, J. H. & Patterson, J. E. (1995). Methicillin-resistant Staphylococcus aureus as a community organism. Clinical Infectious Diseases, 21, 1308–12.
8. Steinberg, J. P., Clark, C. C. and Hackman, B. O. (1996). Nosocomial and community-acquired Staphylococcus aureus bacteremias from 1980 to 1993: impact of intravascular devices and methicillin resistance. Clinical Infectious Diseases, 23, 255–259.
9. Akram, J. & Glatt, A. E. (1998). True community-acquired methicillin-resistant Staphylococcus aureus bacteremia. Infection Control and Hospital Epidemiology, 19(2), 106–107.

10. Kayaba, H., Kodama, K., Tamura, H. & Fujiwara, Y. (1996). The sprezad of methicillin-resistant in a rural community: will it become a common microorganism colonizing among the general population? *Surgery Today*, 27,217–219.
11. Mitchell, J. M., MacCulloch, D. & Morris, A. J. (1996). MRSA in the community. *New Zealand Medical Journal*, 109(1032), 411.
12. Maguire, G. P., Arthur, A. D., Boustead, P. J., Dwyer, B. & Currie, B. J. (1996). Emerging epidemic of community-acquired methicillin-resistant *Staphylococcus aureus* infection in the Northern Territory. *Medical Journal of Australia*, 164, 721–723.
13. Riley, T. V., Pearman, J. W. and Rouse, I. L. (1995). Changing Epidemiology of methicillin-resistant *Staphylococcus aureus* in Western Australia. *The Medical Journal of Australia*, 163, 412–414.
14. Collignon, P., Gosbell, I., Vickery, A., Nimmo, G., Stylianopoulos, T., & Gottlieb, T (1998). Community-acquired methicillin-resistant *Staphylococcus aureus* in Australia. *The Lancet*, 352, 145–146.
15. Maguire, G. P., Arthur, A. D., Boustead, P. J., Dwyer, B. and Currie, B. J. (1998). Clinical experience and outcomes of community-acquired and nosocomial methicillin-resistant *Staphylococcus aureus* in a northern Australian hospital. *Journal of Hospital Infections*, 38, 273–281.
16. Daum, R. S. (1998). Community-acquired methicillin-resistant *Staphylococcus aureus* infections. *Concise Reviews of Pediatric Infectious Diseases*, 17(8), 745–747.
17. Fogel, M. A., Nussbaum, P. B., Feintzeig, I. D. Hunt, W. A., Gavin, J. P. and Kim, R. C. (1998). Cephazolin in chronic hemodialysis patients: a safe, effective alternative to vancomycin. *American Journal of Kidney Diseases*, 32(3), 401–409.
18. Bastone, E. B., Li, S. C., Ioannides-Demos, L. L., Spicer, W. J. & McLean, A. J. (1993). Kill kinetics and regrowth patterns of *Eschericia coli* exposed to gentamicin concentration-time profiles simulating in vivo bolus and infusion dosing. *Antimicrobial Agents and Chemotherapy*, 37(4), 914–917.
19. Gibaldi, M. & Pierrier, D. (1982). *Pharmacokinetics*, 2nd edn. Marcel Dekker Inc. New York.
20. Begg, E. J. & Barclay, M. L. (1995). Aminoglycosides-50 years. *British Journal of Clinical Pharmacology*. 39, 597–603.
21. Wood, P. J., Ioannides-Demos, L. L., Bastone, E. B., Spicer, W. J. & McLean, A. J. (1996). Kill kinetics and regrowth patterns of *Pseudomonas aeruginosa* exposed to concentration-time profiles of tobramycin simulating in vivo infusion and bolus dosing. *Antimicrobial Agents and Chemotherapy*, 40(5), 1321–1324.
22. Ali, M. Z. & Goetz, M. B. (1997). A meta-analysis of the relative efficacy and toxicity of single daily dosing versus multiple daily dosing of aminoglycosides. *Clionical Infectious Diseases* 24, 796–809.
23. Moore, R. D., Lietman, P. S. & Smith, C. R. (1987). Clinical response to aminoglycoside therapy: importance of the ratio of peak concentration to minimal inhibitory concentration. *The Journal of Infectious Diseases*, 155 (1), 93–99.
24. Gerber, A. U,., Wiprachtiger, P., Stettler-Spichiger, U. & Lebek, G. (1982). Constant infusions vs. intermittent doses of gentamicin against *Pseudomonas aeruginosa* in-vitro. *The Journal of Infectious Diseases*, 145(4), 554–560.
25. Rayner, C. R., Ioannides-Demos, L. L, Brien, J. E., Lioloios, L. L. & Spicer, W. J. (1998). Initial concentration-time profile of gentamicin determines efficacy against *Enterobacter cloacae* ATCC 13047. *Antimicrobial Agents and Chemotherapy*, 42(6), 1370–1374.
26. Ioannides-Demos, L. L., Liolios, L. L., Wood, P., Spicer, W. J. & McLean, A. J. (1998). Changes in MIC alter responses to *Pseudomonas aeruginosa* to tobramycin exposure. *Antimicrobial Agents and Chemotherapy*, 42(6) 1365–1369.
27. Ter Braak, E. W., De Vries, P. J., Boutler, K. P., Van Der Vegt, S. G., Dorrestein, G. C., Nortier, J. W., Van Dijk, A., Verkooyen, R. P. & Verbrugh, H. A. (1990). Once-daily dosing regimen for aminoglycoside plus β-lactam combination therapy of serious bacterial infections: comparative trial with netilmicin plus ceftriaxone. *American Journal of Medicine*, 89, 58–65.
28. Kapusnik, J. E., Hackbarth, C. J., Chambers, H. F., Carpenter, T & Sande, M. A. Single, larger, daily dosing versus onternittent dosing of toramycin for treating experimental *Pseudomonas pneumonia*. *Journal of Infectious Diseases*, 158(1), 7–12.
29. Gavalda, J., Cardona, P. J., Almitrante, B., Capdevila, A. J., Laguarda, M., Pou, L., Crespo, E., Pigrau, C. & Pahissa, A. (1996). Treatment of experimental endocarditis due to *Enterococcus faecalis* using once-daily dosing regimen of gentamicin plus simulated profiles of ampicillin human serum. *Antimicrobial Agents and Chemotherapy*, 40(1), 173–178.
30. Bailey, R. R., Begg, E. J., Smith, A. H., Robson, R. A., Lynn, K. L., Chambers, S. T., Barclay, M. L. & Hornibrook, J. (1996). Prospective, randomized, controlled study comparing two dosing regimens of gentamicin/oral ciprofloxacin switch therapy for acute pyelonephritis. *Clinical Nephrology*, 46(3), 183–186.
31. Bailey, T. C., Little, J. R., Littenberg, B., Reichley, R. M. & Dunagan, W. C. (1997). A meta-analysis of extended-internal dosing versus multiple daily dosing of aminoglycosides. *Clinical Infectious Diseases*, 24, 786–795.
32. Cholewka, K. A., Ioannides-Demos, L. L., Liolios, L., Paull, P., Spicer, W. J., and McLean, A. J. (1999). Caphelosporin clinical concentration-time profile modelling and in-vitro bactericidal effects on *Escherichia coli*. *Journal of Antimicrobial Chemotherapy*, 44, 471–476.

TABLE 1

| Gentamicin Post-Distribution Peak followed by maintained cephazolin concentrations | | Bacterial Counts [log10 cfu/mL] | | | |
|---|---|---|---|---|---|
| | | −0.5 h | 2 h | 8 h | 24 h |
| 8 mg/L bolus gentamicin followed by | 0 mg/L | 5.87 ± 0.35 | 1.32 ± 0.69 | 4.91 ± 0.70 | 8.88 ± 0.11 |
| | 0.5 mg/L | 5.86 ± 0.05 | 2.53 ± 2.01 | 5.28 ± 0.65 | 8.94 ± 0.09 |
| | 1.0 mg/L | 6.06 ± 0.08 | 1.43 ± 0.87 | 5.57 ± 0.59 | 8.97 ± 0.20 |

TABLE 1-continued

| Gentamicin Post-Distribution Peak followed by maintained cephazolin concentrations | | Bacterial Counts [log10 cfu/mL] | | | |
|---|---|---|---|---|---|
| | | −0.5 h | 2 h | 8 h | 24 h |
| a cephazolin | 2.0 mg/L | 6.00 ± 0.14 | 0.98 ± 0.78 | 2.87 ± 0.40 | 6.24 ± 0.66 |
| trough of: | 4.0 mg/L | 6.02 ± 0.07 | 0.65 ± 0.71 | NGD | NGD |
| 12 mg/L bolus | 0 mg/L | 6.10 ± 0.26 | 0.69 ± 0.87 | 4.54 ± 1.15 | 8.80 ± 0.05 |
| gentamicin | 0.5 mg/L | 5.87 ± 0.04 | 0.48 ± 0.76 | 4.66 ± 0.95 | 8.81 ± 0.06 |
| followed by | 1.0 mg/L | 5.94 ± 0.10 | 0.43 ± 0.67 | 1.16 ± 1.34 | 8.33 ± 1.10 |
| a cephazolin | 2.0 mg/L | 5.93 ± 0.20 | 0.22 ± 0.53 | NGD | NGD |
| trough of: | 4.0 mg/L | 5.95 ± 0.09 | 0.22 ± 0.53 | NGD | NGD |
| 16 mg/L bolus | 0 mg/L | 5.85 ± 0.050 | 0.48 ± 0.76 | 3.85 ± 1.24 | 8.79 ± 0.05 |
| gentamicin | 0.5 mg/L | 5.78 ± 0.028 | NGD | 3.31 ± 0.91 | 8.84 ± 0.03 |
| followed by | 1.0 mg/L | 5.88 ± 0.030 | 0.22 ± 0.53 | 1.12 ± 1.25 | 8.82 ± 0.04 |
| a cephazolin | 2.0 mg/L | 5.83 ± 0.030 | NGD | NGD | NGD |
| trough of: | 4.0 mg/L | 5.89 ± 0.030 | NGD | NGD | NGD |
| 20 mg/L bolus | 0 mg/L | 5.89 ± 0.03 | NGD | 3.15 ± 0.734 | 8.81 ± 0.04 |
| gentamicin | 0.5 mg/L | 5.87 ± 0.06 | NGD | 2.95 ± 1.38 | 8.79 ± 0.05 |
| followed by | 1.0 mg/L | 5.85 ± 0.03 | NGD | 0.64 ± 1.07 | 5.73 ± 3.66 |
| a cephazolin | 2.0 mg/L | 5.81 ± 0.05 | NGD | NGD | NGD |
| trough of: | 4.0 mg/L | 5.87 ± 0.04 | NGD | NGD | NGD |

TABLE 2

| Maintained Cephazolin Concentrations | Bacterial Count [log 10 u/mL] | | | |
|---|---|---|---|---|
| | 0 h | 2 h | 8 h | 24 h |
| Control | 5.91 ± 0.10 | 7.36 ± 0.45 | 8.76 ± 0.07 | 8.84 ± 0.06 |
| 0.5 mg/L | 5.88 ± 0.09 | 7.43 ± 0.28 | 8.67 ± 0.24 | 8.82 ± 0.06 |
| 1.0 mg/L | 5.83 ± 0.29 | 6.21 ± 0.76 | 8.59 ± 0.35 | 8.79 ± 0.05 |
| 2.0 mg/L | 5.88 ± 0.07 | 3.70 ± 0.32 | 4.98 ± 0.34 | 8.79 ± 0.05 |
| 4.0 mg/L | 5.88 ± 0.06 | 3.61 ± 0.22 | 4.38 ± 0.42 | 6.14 ± 0.93 |
| 12.5 mg/L | 5.85 ± 0.14 | 3.11 ± 0.26 | 2.18 ± 0.63 | 4.77 ± 1.89 |
| 50 mg/L | 5.93 ± 0.11 | 2.17 ± 0.39 | 1.55 ± 0.93 | 1.56 ± 1.14 |
| 75 mg/L | 5.82 ± 0.23 | 2.09 ± 0.29 | 1.11 ± 0.96 | 1.05 ± 1.23 |
| 100 mg/L | 5.85 ± 0.08 | 2.01 ± 0.26 | 0.86 ± 0.95 | 0.70 ± 0.78 |
| 200 mg/L | 5.86 ± 0.04 | 2.16 ± 0.24 | 0.78 ± 0.87 | 1.43 ± 0.74 |
| 250 mg/L | 5.81 ± 0.03 | 1.82 ± 0.44 | 1.22 ± 0.96 | 1.61 ± 0.86 |

TABLE 4

| | Trough gentamicin concentration in broth | | | | | |
|---|---|---|---|---|---|---|
| Exposure time to maintained concentration of gentamicin | 0 mg/L | 0.5 mg/L | 1.0 mg/L | 2.0 mg/L | 3.0 mg/L | 4.0 mg/L |
| 1 hr | + | + | − | − | − | − |
| 2 hr | + | + | − | − | − | − |
| 3 hr | + | + | − | − | − | − |
| 4 hr | ++ | + | − | − | − | − |
| 8 hr | +++ | ++ | − | − | − | − |
| 24 hr | +++ | +++ | − | − | − | − |
| 48 hr | +++ | +++ | − | − | − | − |

The claims defining the invention are as follows:

1. A method of treating bacterial infection caused by methicillin resistant *staphylococcus aureus*, comprising the step of administering to a subject an antibacterial agent

TABLE 3

| Gentamicin Profile | $C_{max}$ (mg/liter) | $C_{min}$ (mg/liter) | AUC 0–49 h (mg.hr/liter) | BACTERIAL COUNTS log $^{10}$ (CFU/mL) | | | |
|---|---|---|---|---|---|---|---|
| | | | | 3 hr | 11 hr | 25 hr | 49 hr |
| *Post-distribution peak of 4 mg/liter then reconstituted at 1 hr to: | | | | | | | |
| 0 mg/liter | 6.22 ± 0.33 | 0 | 3.97 ± 0.09 | 3.96 ± 0.70 | 9.24 ± 0.34 | 9.15 ± 0.17 | 8.93 ± 0.12 |
| 2.0 mg/liter | 6.32 ± 0.25 | 1.93 ± 0.24 | 102.66 ± 6.91 | 1.92 ± 1.21 NS | 7.76 ± 1.06 p = 0.01 | 8.69 ± 0.63 NS | 9.34 ± 0.27 NS |
| 2.5 mg/liter | 6.23 ± 0.23 | 2.47 ± 0.31 | 124.40 ± 4.27 | 0.33 ± 0.52 p = 0.01 | 0.33 ± 0.52 p = 0.01 | 4.85 ± 3.82 p = 0.01 | 5.98 ± 4.63 NS |
| 3.0 mg/liter | 6.28 ± 0.37 | 2.88 ± 0.23 | 153.43 ± 11.01 | 0.33 ± 0.52 p = 0.01 | NGD p < 0.01 | NGD p < 0.01 | NGD p < 0.01 |
| **Post-distribution peak of 4 mg/liter then reconstituting to 3.0 mg/liter at 1 hr and maintaining for: | | | | | | | |
| 0 hr (control) | 6.12 ± 0.35 | 0 | 3.93 ± 0.33 | 3.05 ± 0.33 | 8.89 ± 0.20 | 9.07 ± 0.12 | 9.01 ± 0.06 |
| 2 hr | 6.23 ± 0.27 | 2.45 ± 0.24 | 124.98 ± 3.08 | 0.17 ± 0.41 p < 0.01 | 0.55 ± 0.61 p = 0.01 | 7.95 ± 0.54 p = 0.01 | 8.89 ± 0.19 NS |
| 4 hr | 6.30 ± 0.45 | 2.37 ± 0.34 | 120.99 ± 6.05 | 0.17 ± 0.41 p < 0.01 | 0.17 ± 0.41 p < 0.01 | 5.18 ± 4.02 p = 0.01 | 5.99 ± 4.64 p = 0.03 |
| 8 hr | 6.37 ± 0.22 | 2.35 ± 0.19 | 119.78 ± 8.84 | 0.33 ± 0.52 p < 0.01 | NGD p < 0.01 | NGD p < 0.01 | NGD p < 0.01 | active on bacterial cell wall together with an aminoglycoside to attain a peak concentration of 4 to 18 mg/l of aminoglycoside and thereafter maintaining the aminoglycoside at a concentration of 1 to 4 mg/l for at least 1 hour; wherein said aminoglycoside potentiates the activity of said antibacterial agent.

2. A method according to claim 1, wherein the aminoglycoside concentration peaks at 30–240 minutes after administration of said aminoglycoside.

3. A method according to claim 1, wherein the concentration of the aminoglycoside is maintained at 1–4 mg/l for up to 16 hours.

4. A method according to claim 1, wherein the concentration of antibacterial agent is maintained at 2 mg/l or more while the aminoglycoside is maintained at 1–4 mg/l.

5. A method according to claim 4, wherein the concentration of the antibacterial agent is maintained at about 2 mg/l for at least about 8 to 24 hours after the concentration of the aminoglycoside declines to a negligible level.

6. A method according to claim 1, wherein the antibacterial agent active on bacterial cell wall is a cephalosporin or cephamycin.

7. A method according to claim 6, wherein the antibacterial agent is selected from the group consisting of cephalosporin, cephalothin, cephaloridine, cephalexin, cephaglycin, cephradine, cefaclor, cefoxitin, cefamandole, cefotaxime, ceftriaxone, ceftazidime and cefotetan.

8. A method according to claim 1, wherein the antibacterial agent active on bacterial cell wall is a β-lactam antibiotic.

9. A method according to claim 1, wherein the aminoglycoside is selected from the group consisting of gentamicin, tobramycin, netilimicin, amikacin and streptomycin.

10. A sustained-release composition, for treatment of bacterial infection, comprising an aminoglycoside and an antibacterial agent active on bacterial cell wall, wherein the peak concentration of said aminoglycoside is 4 to 18 mg/l and is thereafter maintained at a concentration of 1–4 mg/l for at least 1 hour following administration to a subject in need of such treatment, so as to potentiate the activity of said antibacterial agent.

11. A composition according to claim 10, wherein said composition is for oral, intramuscular or intravenous use.

12. A composition according to claim 10, wherein said composition is implantable.

* * * * *